(12) United States Patent
Facchetti et al.

(10) Patent No.: US 8,569,501 B2
(45) Date of Patent: Oct. 29, 2013

(54) SEMICONDUCTOR MATERIALS AND METHODS OF PREPARATION AND USE THEREOF

(75) Inventors: Antonio Facchetti, Chicago, IL (US); Zhihua Chen, Skokie, IL (US); Florian Doetz, Singapore (SG); Marcel Kastler, Basel (CH); Tobin J. Marks, Evanston, IL (US); He Yan, Skokie, IL (US); Yan Zheng, Skokie, IL (US)

(73) Assignees: BASF SE, Ludwigshafen (DE); Polyera Corporation, Skokie, IL (US)

( * ) Notice: Subject to any disclaimer, the term of this patent is extended or adjusted under 35 U.S.C. 154(b) by 270 days.

(21) Appl. No.: 12/994,596

(22) PCT Filed: May 29, 2009

(86) PCT No.: PCT/EP2009/056624
§ 371 (c)(1),
(2), (4) Date: Feb. 17, 2011

(87) PCT Pub. No.: WO2009/144302
PCT Pub. Date: Dec. 3, 2009

(65) Prior Publication Data
US 2011/0136333 A1      Jun. 9, 2011

Related U.S. Application Data

(60) Provisional application No. 61/057,547, filed on May 30, 2008.

(51) Int. Cl.
*C07D 471/08* (2006.01)
*H01L 51/50* (2006.01)

(52) U.S. Cl.
USPC ............................................ 546/37; 313/504

(58) Field of Classification Search
USPC ............................................ 546/37; 313/504
See application file for complete search history.

(56) References Cited

U.S. PATENT DOCUMENTS

| | | | |
|---|---|---|---|
| 5,086,059 A | 2/1992 | Ardecky et al. | |
| 5,641,782 A | 6/1997 | Sun et al. | |
| 5,645,965 A * | 7/1997 | Duff et al. | 430/58.8 |
| 2007/0219375 A1 | 9/2007 | Fujiyama et al. | |
| 2008/0167435 A1 | 7/2008 | Marks et al. | |
| 2008/0177073 A1 | 7/2008 | Faccheti et al. | |
| 2008/0185577 A1 | 8/2008 | Faccheti et al. | |
| 2008/0188660 A1 | 8/2008 | Pschirer et al. | |
| 2008/0287678 A1 | 11/2008 | Konemann | |

FOREIGN PATENT DOCUMENTS

| | | |
|---|---|---|
| EP | 1 736 476 | 12/2006 |
| WO | 91 18884 | 12/1991 |
| WO | 96 25400 | 8/1996 |
| WO | 2006 060533 | 6/2006 |
| WO | 2006 111511 | 10/2006 |
| WO | 2007 014902 | 2/2007 |
| WO | 2008 139452 | 11/2008 |

OTHER PUBLICATIONS

U.S. Appl. No. 13/128,961, filed May 12, 2011, Quinn, et al.
U.S. Appl. No. 13/140,595, filed Jun. 17, 2011, Mishra, et al.
Tang, C.W., "Two-layer organic photovoltaic cell," Appl. Phys. Lett., vol. 48, No. 2, pp. 183-185, (Jan. 13, 1986).
Law, K.-Y., "Organic Photoconductive Materials: Recent Trends and Developments," Chem. Rev., vol. 93, pp. 449-486, (1993).
Forrest, S.R., "Ultrathin Organic Films Grown by Organic Molecular Beam Deposition and Related Techniques," Chem. Rev., vol. 97, pp. 1793-1896, (1997).
International Search Report issued Aug. 10, 2009 in PCT/EP09/056624 filed May 29, 2009.
U.S. Appl. No. 61/057,547, filed May 30, 2008, Chen, et al.
U.S. Appl. No. 61/026,311, filed Feb. 5, 2008, Doetz, et al.
U.S. Appl. No. 61/026,322, filed Feb. 5, 2008, Chen, et al.
U.S. Appl. No. 61/050,010, filed May 2, 2008, Chen, et al.
U.S. Appl. No. 61/088,215, filed Aug. 12, 2008, Chen, et al.
U.S. Appl. No. 61/088,236, filed Aug. 12, 2008, Chen, et al.
U.S. Appl. No. 61/088,246, filed Aug. 12, 2008, Chen, et al.
U.S. Appl. No. 60/859,761, filed Nov. 17, 2006, Yan, et al.
U.S. Appl. No. 60/879,145, filed Jan. 8, 2007, Facchetti, et al.
U.S. Appl. No. 13/266,935, filed Oct. 28, 2011, Karpov, et al.

* cited by examiner

*Primary Examiner* — Charanjit Aulakh
(74) *Attorney, Agent, or Firm* — Oblon, Spivak, McClelland, Maier & Neustadt, L.L.P.

(57) ABSTRACT

Disclosed are new semiconductor materials prepared from dimeric perylene compounds. Such compounds can exhibit high n-type carrier mobility and/or good current modulation characteristics. In addition, the compounds of the present teachings can possess certain processing advantages such as solution-processability and/or good stability at ambient conditions.

24 Claims, 5 Drawing Sheets

SEMICONDUCTOR MATERIALS AND METHODS OF PREPARATION AND USE THEREOF

CROSS REFERENCE TO RELATED APPLICATION

This application claims priority to and the benefit of U.S. Provisional Patent Application Ser. No. 61/057,547, filed on May 30, 2008, the disclosure of which is incorporated by reference herein in its entirety.

BACKGROUND

A new generation of optoelectronic devices such as organic thin film transistors (TFT), organic light emitting diodes (OLEDs), printable circuits, organic photovoltaic devices, capacitors and sensors are built upon organic semiconductors as their active components. These devices need to achieve performance compatible with their envisioned applications such as display backplanes, radio-frequency identification tags, printed sensors and photovoltaics. Like inorganic material-based electronics, organic semiconductor-based devices can operate efficiently and at high speed if both p-type and n-type semiconductor materials exhibit high charge carrier mobility and stability under ambient conditions, and can be processed in a cost-effective manner.

The most promising organic semiconductors include π-conjugated small molecules and polymers that have an electronic structure compatible with efficient charge transport and suitable for charge injection from the electrical contacts. To date, most of the organic semiconductors that have been investigated and optimized are p-type semiconductor materials due to their enhanced environmental stability. In contrast, n-type semiconductors are limited to a small number of molecules and polymers, most of which are inactive under ambient conditions. It has been reported that some core-cyanated rylenes, including perylenes, anthracenes, naphthalenes, and the like, can be active under ambient-conditions and can exhibit processing versatility. See e.g., Tang, C. W. (1986), Appl. Phys. Lett., 48: 183; Law, K. Y. (1993), Chem. Rev., 93: 449; and Forrest, R. F. (1997), Chem. Rev., 97: 1793.

While both contact and noncontact printing techniques have been employed for the fabrication of electronic devices, wider application of organic semiconductor materials in printable circuits has been constrained by the unavailability of suitable formulations. For example, satisfactory printing results only can be obtained if these materials can be formulated in printing medium with appropriate viscosity. In some instances, inclusion of binders is not a feasible option because of their negative impact on the carrier mobility of the semiconductor materials.

Accordingly, the art desires new n-type organic semiconductor materials, especially those that can be formulated in solutions of a broad viscosity range suitable for use in various solution processing techniques including, but not limited to, contact and noncontact printing.

SUMMARY

In light of the foregoing, the present teachings provide organic semiconductor materials and associated devices that can address various deficiencies and shortcomings of the prior art, including those outlined above.

More specifically, the present teachings provide organic semiconductor materials that are based upon dimeric rylene compounds, including dimeric perylene compounds. It has been found that compounds of the present teachings can afford useful electrical properties and broad viscosity ranges suitable for various solution-phase processes.

In one aspect, the present teachings provide compounds having Formula I:

wherein Q and Q' independently are optionally substitued rylene moieties and L is a linker as described herein.

The present teachings also provide methods of preparing such compounds and semiconductor materials as well as various compositions, articles, structures, and devices that include the compounds and semiconductor materials disclosed herein.

The foregoing and other features and advantages of the present teachings will be more fully understood from the following schemes, figures, tables, description, and claims.

BRIEF DESCRIPTION OF DRAWINGS

It should be understood that the drawings described below are for illustration purpose only. The drawings are not necessarily to scale and are not intended to limit the scope of the present teachings in any way.

DETAILED DESCRIPTION

Figure 1:
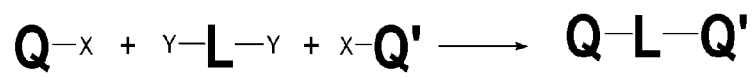
FIG. 1 shows a general synthetic scheme of preparing compounds of the present teachings.

The present teachings provide organic semiconductor materials, including compounds and compositions. The organic semiconductor materials disclosed herein can exhibit useful electrical properties and can be solution-processable, e.g., spin-coatable and printable. In addition, these materials can be considered n-type semiconductor materials and can be used to fabricate various organic electronic articles, structures and devices, including field-effect transistors, unipolar circuitries, complementary circuitries, photovoltaic devices, and light emitting devices.

Specifically, the present teachings provide dimeric rylene compounds, including dimeric perylene compounds. These compounds typically can have some solubility in one or more common solvents and can be stable under ambient conditions.

The present teachings also provide methods of preparing and using these compounds, including compositions, articles, structures, and devices that can include such compounds.

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

As used herein, "solution-processable" refers to compounds (e g , dimeric perylene compounds), materials, or compositions that can be used in various solution-phase processes including spin-coating, printing (e.g., inkjet printing, screen printing, pad printing, offset printing, gravure printing, flexographic printing, lithographic printing, and the like), spray coating, electrospray coating, drop casting, dip coating, and blade coating.

As used herein, a "cyclic moiety" can include one or more (e.g., 1-6) carbocyclic or heterocyclic rings. In embodiments where the cyclic moiety is a polycyclic moiety, the polycyclic system can include one or more rings fused to each other (i.e., sharing a common bond) and/or connected to each other via a spiro atom. The cyclic moiety can be a cycloalkyl group, a cycloheteroalkyl group, an aryl group, or a heteroaryl group, and can be substituted as disclosed herein. As used herein, "bispolycyclic" or "bispolycyclic compound" refers to a molecule including two polycyclic moieties connected by a covalent bond or a divalent group. The polycyclic moieties in the bispolycyclic compounds can be identical or different and each of the polycyclic moieties optionally can be substituted as disclosed herein.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly π-conjugated and can include polycyclic aromatic hydrocarbons such as rylenes having the formula:

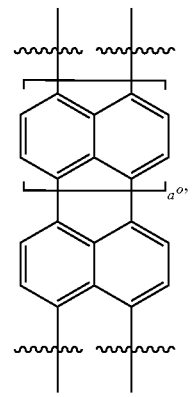

where $a^o$ can be an integer in the range of 0-3; coronenes having the formula:

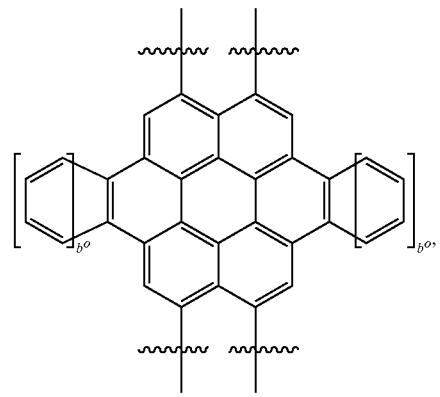

where $b^o$ can be an integer in the range of 0-3; and linear acenes having the formula:

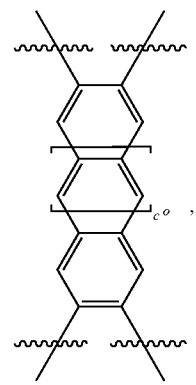

where $c^o$ can be an integer in the range of 0-4. The fused ring moiety can be substituted as disclosed herein.

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$alkyl group), for example, 1-20 carbon atoms (i.e., $C_{1-20}$alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$haloalkyl group), for example, 1 to 20 carbon atoms (i.e., $C_{1-20}$haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula —$C_zH_{2z+1-t}X^0_t$, where $X^0$, at each occurrence, is F, Cl, Br or I, z is an integer in the range of 1 to 40, and t is an integer in the range of 1 to 81, provided that t is less than or equal to 2z+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxyl, hexoxyl groups, and the like. The alkyl group in the —O-alkyl group can be substituted as described herein.

As used herein, "alkylthio" refers to an —S-alkyl group (which, in some cases, can be expressed as —$S(O)_w$-alkyl, wherein w is 0). Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "arylalkyl" refers to an -alkyl-aryl group, where the arylalkyl group is covalently linked to the defined chemical structure via the alkyl group. An arylalkyl group is within the definition of a —Y—$C_{6-14}$aryl group, where Y is as defined herein. An example of an arylalkyl group is a benzyl group (—$CH_2$—$C_6H_5$). An arylalkyl group can be optionally substituted, i.e., the aryl group and/or the alkyl group, can be substituted as disclosed herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$alkenyl group), for example, 2 to 20 carbon atoms (i.e., $C_{2-20}$alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., $C_{2-40}$alkynyl group), for example, 2 to 20 carbon atoms (i.e., $C_{2-20}$alkynyl group). In some embodiments, alkynyl groups can be substituted as described herein. An alkynyl group is generally not substituted with another alkynyl group, an alkyl group, or an alkenyl group.

As used herein, "cycloalkyl" refers to a non-aromatic carbocyclic group including cyclized alkyl, alkenyl, and alkynyl groups. In various embodiments, a cycloalkyl group can have 3 to 24 carbon atoms, for example, 3 to 20 carbon atoms (e.g., $C_{3-14}$cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as described herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 24 ring atoms, for example, 3 to 20 ring atoms (e.g., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_{6-20}$aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/ aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

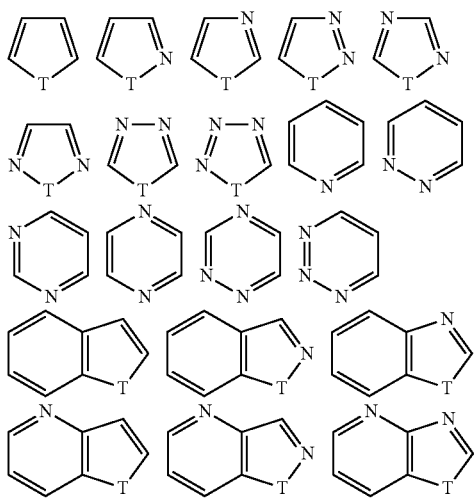

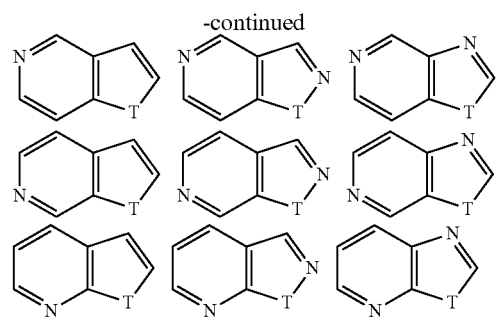

where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

Compounds of the present teachings can include a "divalent group" defined herein as a linking group capable of forming a covalent bond with two other moieties. For example, compounds of the present teachings can include a divalent $C_{1-20}$alkyl group, such as, for example, a methylene group; a divalent $C_{2-20}$alkenyl group, such as, for example, a vinylene group; a divalent $C_{2-20}$alkynyl group, such as, for example, an ethynylene group; a divalent $C_{6-14}$aryl group, such as, for example, a phenylene group; a divalent 3-14 membered cycloheteroalkyl group, such as, for example, a pyrrolidylene; or a divalent 5-14 membered heteroaryl group, such as, for example, a thiophenylene group.

The electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein.

It should be understood that the term "electron-accepting group" can be used synonymously herein with "electron acceptor" and "electron-withdrawing group". In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halo (e.g., F, Cl, Br, I), —$NO_2$, —CN, —NC, —$S(R^o)_2{}^+$, —$N(R^o)_3{}^+$, —$SO_3H$, —$SO_2R^o$, —$SO_3R^o$, —$SO_2NHR^o$, —$SO_2N(R^o)_2$, —COOH, —$COR^o$, —$COOR^o$, —$CONHR^o$, —$CON(R^o)_2$, $C_{1-40}$haloalkyl groups, $C_{6-14}$aryl groups, and 5-14 membered electron-poor heteroaryl groups; where $R^o$ is a $C_{1-20}$alkyl group, a $C_{2-20}$alkenyl group, a $C_{2-20}$alkynyl group, a $C_{1-20}$haloalkyl group, a $C_{1-20}$alkoxy group, a $C_{6-14}$aryl group, a $C_{3-14}$cycloalkyl group, a 3-14 membered cycloheteroalkyl group, and a 5-14 membered heteroaryl group, each of which optionally can be substituted as described herein. For example, each of the $C_{1-20}$alkyl group, the $C_{2-20}$alkenyl group, the $C_{2-20}$alkynyl group, the $C_{1-20}$haloalkyl group, the $C_{1-20}$alkoxy group, the $C_{6-14}$aryl group, the $C_{3-14}$cycloalkyl group, the 3-14 membered cycloheteroalkyl group, and the 5-14 membered heteroaryl group optionally can be substituted with 1-5 small electron-withdrawing groups such as F, Cl, Br, —$NO_2$, —CN, —NC, —$S(R^o)_2{}^+$, —$N(R^o)_3{}^+$, —$SO_3H$, —$SO_2R^o$, —$SO_3R^o$, —$SO_2NHR^o$, —$SO_2N(R^o)_2$, —COOH, —$COR^o$, —$COOR^o$, —$CONHR^o$, and —$CON(R)_2$.

It should be understood that the term "electron-donating group" can be used synonymously herein with "electron donor". In particular, an "electron-donating group" or an "electron-donor" refers to a functional group that donates electrons to a neighboring atom more than a hydrogen atom would if it occupied the same position in a molecule. Examples of electron-donating groups include —OH, —$OR^o$, —$NH_2$, —$NHR^o$, —$N(R^o)_2$, and 5-14 membered electron-rich heteroaryl groups, where $R^o$ is a $C_{1-20}$alkyl group, a $C_{2-20}$alkenyl group, a $C_{2-20}$alkynyl group, a $C_{6-14}$aryl group, or a $C_{3-14}$cycloalkyl group.

Various unsubstituted heteroaryl groups can be described as electron-rich (or π-excessive) or electron-poor (or π-deficient). Such classification is based on the average electron density on each ring atom as compared to that of a carbon atom in benzene. Examples of electron-rich systems include 5-membered heteroaryl groups having one heteroatom such as furan, pyrrole, and thiophene; and their benzofused counterparts such as benzofuran, benzopyrrole, and benzothiophene. Examples of electron-poor systems include 6-membered heteroaryl groups having one or more heteroatoms such as pyridine, pyrazine, pyridazine, and pyrimidine; as well as their benzofused counterparts such as quinoline, isoquinoline, quinoxaline, cinnoline, phthalazine, naphthyridine, quinazoline, phenanthridine, acridine, and purine. Mixed heteroaromatic rings can belong to either class depending on the type, number, and position of the one or more heteroatom(s) in the ring. See Katritzky, A. R and Lagowski, J. M., Heterocyclic Chemistry (John Wiley & Sons, New York, 1960).

At various places in the present specification, substituents are disclosed in groups or in ranges. It is specifically intended that the description include each and every individual subcombination of the members of such groups and ranges. For example, the term "$C_{1-6}$alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes and imines). It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan.

It is specifically contemplated that the depiction of one regioisomer includes any other regioisomers and any regioisomeric mixtures unless specifically stated otherwise. For example, perylene-based compounds of the present teachings can include any perylene derivatives in their pure form or mixtures thereof, where the perylene derivatives can be substituted with 1, 2, 3, 4, 5, 6, 7, or 8 substituents. Specifically, the perylene derivatives can include compounds having the moiety:

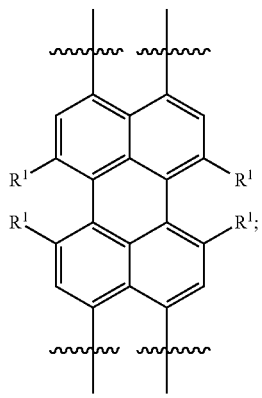

where $R^1$, at each occurrence, independently can be H or a substitution group (e.g., an electron-withdrawing group or a leaving group). In various embodiments, two of the $R^1$ groups can be H and the other two $R^1$ groups independently can be an electron-withdrawing group or a leaving group. Accordingly, in the embodiments where two of the $R^1$ groups are H and the other two independently are an electron-withdrawing group or a leaving group, compounds of the present teachings can have regioisomers having the formulae:

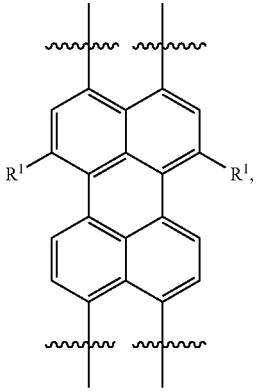

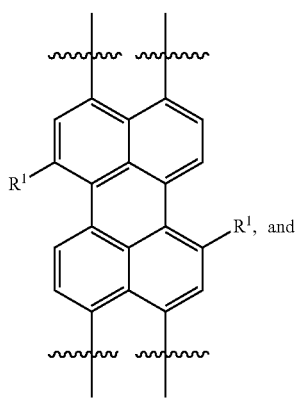

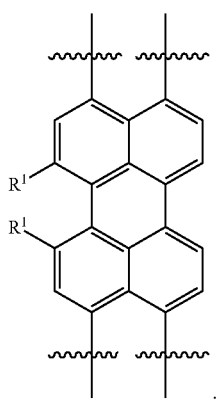

In certain embodiments, compounds of the present teachings can include compounds having formula i or ii:

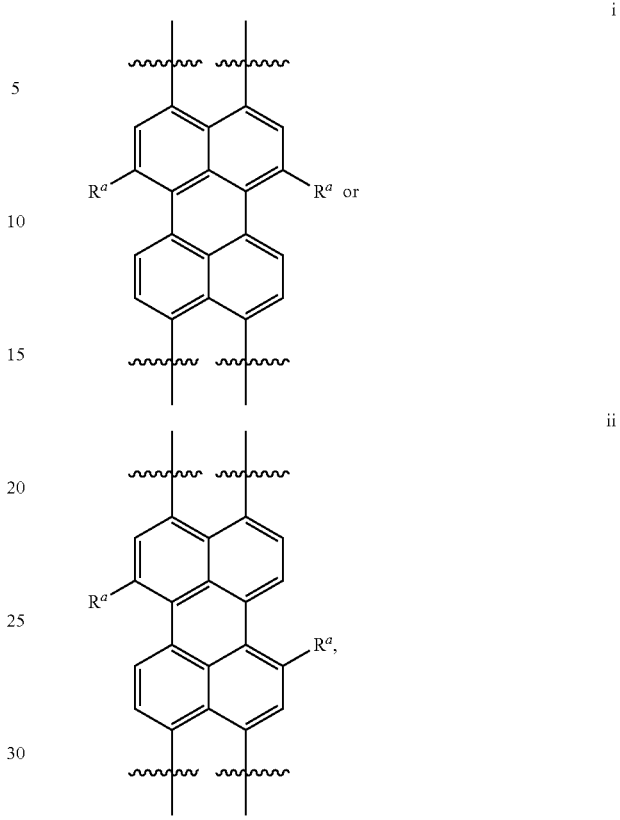

or mixtures thereof, where $R^a$ is as defined herein, for example, halogen (e.g., Br) or CN. Further, it is specifically contemplated that the depiction of one regioisomer includes any other regioisomers and any regioisomeric mixtures unless specifically stated otherwise. Accordingly, for example, the use of compounds of formula i include compounds of formula ii (and vice versa) and mixtures of compounds of formulae i and ii.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide ($N_3$), thiocyanate (SCN), nitro ($NO_2$), cyanate (CN), water ($H_2O$), ammonia ($NH_3$), and sulfonate groups (e.g., $OSO_2$—R, wherein R can be a $C_{1-10}$alkyl group or a $C_{6-14}$aryl group each optionally substituted with 1-4 groups independently selected from a $C_{1-10}$alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

As used herein, a "p-type semiconductor material" or a "donor" material refers to a semiconductor material having holes as the majority current or charge carriers. In some embodiments, when a p-type semiconductor material is deposited on a substrate, it can provide a hole mobility in excess of about $10^{-5}$ cm$^2$/Vs. In the case of field-effect devices, a p-type semiconductor can also exhibit a current on/off ratio of greater than about 10.

As used herein, an "n-type semiconductor material" or an "acceptor" material refers to a semiconductor material having electrons as the majority current or charge carriers. In some embodiments, when an n-type semiconductor material is deposited on a substrate, it can provide an electron mobility in excess of about $10^{-5}$ cm$^2$/Vs. In the case of field-effect devices, an n-type semiconductor can also exhibit a current on/off ratio of greater than about 10.

As used herein, "mobility" refers to a measure of the velocity with which charge carriers, for example, holes (or units of positive charge) in the case of a p-type semiconductor material and electrons (or units of negative charge) in the case of an n-type semiconductor material, move through the material under the influence of an electric field. This parameter, which depends on the device architecture, can be measured using a field-effect device or space-charge limited current measurements.

As used herein, a compound can be considered "ambient stable" or "stable at ambient conditions" when the carrier mobility or the reduction-potential of the compound is maintained at about its initial measurement when the compound is exposed to ambient conditions, for example, air, ambient temperature, and humidity, over a period of time. For example, a compound can be described as ambient stable if its carrier mobility or reduction potential does not vary more than 20% or more than 10% from its initial value after exposure to ambient conditions, including, air, humidity and temperature, over a 3 day, 5 day, or 10 day period.

In one aspect, the present teachings provide bispolycyclic compounds having Formula I:

Q-L-Q'  I wherein:
Q and Q' independently are selected from:

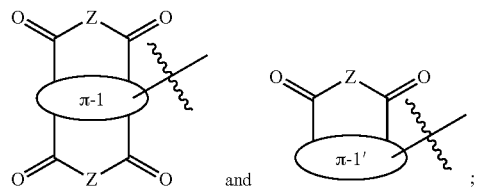

and

L is a linker;
wherein π-1 and π-1' independently are a fused ring moiety optionally substituted with 1-8 $R^a$ groups;

Z, at each occurrence, is selected from a) O, b) S, c) NR$^b$, d) C(O), and e) CR$^e$R$^d$;

$R^a$, at each occurrence, is a) halogen, b) —CN, c) —NO$_2$, d) —OR$^f$, e) —SR; f) —NR$^g$R$^h$, g) —N(O)R$^g$H$^h$, h) —S(O)$_m$R$^g$, i) —S(O)$_m$OR$^g$, j) —S(O)$_m$NR$^g$R$^h$, k) —C(O)R$^g$, l) —C(O)OR$^f$, m) —C(O)NR$^g$R$^h$, n) —C(S)NR$^g$R$^h$, o) —SiH$_3$, p) —SiH(C$_{1-20}$alkyl)$_2$, q) —SiH$_2$(C$_{1-20}$alkyl), r) —Si(C$_{1-20}$alkyl)$_3$, s) a C$_{1-20}$alkyl group, t) a C$_{2-20}$alkenyl group, u) a C$_{2-20}$alkynyl group, v) a C$_{1-20}$haloalkyl group, w) a —Y—C$_{3-14}$cycloalkyl group, x) a —Y—C$_{6-14}$ aryl group, y) a —Y-3-14 membered cycloheteroalkyl group, or z) a —Y-5-14 membered heteroaryl group, wherein each of the C$_{1-20}$alkyl group, the C$_{2-20}$alkenyl group, the C$_{2-20}$ alkynyl group, the C$_{3-14}$cycloalkyl group, the C$_{6-14}$aryl group, the 3-14 membered cycloheteroalkyl group, and the 5-14 membered heteroaryl group optionally is substituted with 1-4 $R^1$ groups;

$R^b$, at each occurrence, is a) H, b) —(CH$_2$CH$_2$O)$_q$H, c) —(CH$_2$CH$_2$O)$_q$—CH$_3$, d) —C(O)OR$^f$, e) —C(O)R$^g$, f) —C(O)NR$^g$R$^h$, g) —C(S)OR$^f$, h) —C(S)R$^g$, i) —C(S)NR$^g$R$^h$, j) —S(O)$_m$R$^g$, k) —S(O)$_m$OR$^g$, l) a C$_{1-20}$alkyl group, m) a C$_{2-20}$alkenyl group, n) a C$_{2-20}$alkynyl group, o) a C$_{1-20}$alkoxy group, p) a —Y—C$_{3-14}$cycloalkyl group, q) a —Y—C$_{6-14}$aryl group, r) a —Y-3-14 membered cycloheteroalkyl group, or s) a —Y-5-14 membered heteroaryl group, wherein each of the C$_{1-20}$alkyl group, the C$_{2-20}$alkenyl group, the C$_{2-20}$alkynyl group, the C$_{1-20}$ alkoxy group, the C$_{3-14}$cycloalkyl group, the C$_{6-14}$aryl group, the 3-14 membered cycloheteroalkyl group, and the 5-14 membered heteroaryl group optionally is substituted with 1-4 $R^i$ groups;

$R^c$ and $R^d$, at each occurrence, independently are a) H, b) halogen, c) —(CH$_2$CH$_2$O)$_q$H, d) —(CH$_2$CH$_2$O)$_q$—CH$_3$, e) a C$_{1-20}$alkoxy group, f) a C$_{1-20}$alkyl group, g) a C$_{2-20}$alkenyl group, h) a C$_{2-20}$alkynyl group, i) a —Y—C$_{3-14}$cycloalkyl group, j) a —Y—C$_{6-14}$aryl group, k) a —Y-3-14 membered cycloheteroalkyl group, or l) a —Y-5-14 membered heteroaryl group, wherein each of the C$_{1-20}$alkyl group, the C$_{2-20}$alkenyl group, the C$_{2-20}$alkynyl group, the C$_{3-14}$ cycloalkyl group, the C$_{6-14}$aryl group, the 3-14 membered cycloheteroalkyl group, and the 5-14 membered heteroaryl group optionally is substituted with 1-4 $R^i$ groups;

$R^f$, at each occurrence, is a) H, b) —C(O)R$^g$, c) —C(O) NR$^g$R$^h$, d) —C(S)R$^g$, e) —C(S)NR$^g$R$^h$, f) a C$_{1-20}$alkyl group, g) a C$_{2-20}$alkenyl group, h) a C$_{2-20}$alkynyl group, i) a C$_{3-14}$cycloalkyl group, j) a C$_{6-14}$aryl group, k) a 3-14 membered cycloheteroalkyl group, or l) a 5-14 membered heteroaryl group, wherein each of the C$_{1-20}$alkyl group, the C$_{2-20}$alkenyl group, the C$_{2-20}$alkynyl group, the C$_{3-14}$cycloalkyl group, the C$_{6-14}$aryl group, the 3-14 membered cycloheteroalkyl group, and the 5-14 membered heteroaryl group optionally is substituted with 1-4 $R^i$ groups;

$R^g$ and $R^h$, at each occurrence, independently are a) H, b) —OH, c) —SH, d) —S(O)$_2$OH, e) —C(O)OH, f) —C(O)NH$_2$, g) —C(S)NH$_2$, h) —OC$_{1-10}$alkyl, i) —C(O)—C$_{1-20}$alkyl, j) —C(O)—OC$_{1-20}$alkyl, k) —C(S)N(C$_{1-20}$alkyl)$_2$, l) —C(S)NH—C$_{1-20}$alkyl, m) —C(O)NH—C$_{1-20}$alkyl, n) —C(O)N(C$_{1-20}$alkyl)$_2$, o) —S(O)$_m$—C$_{1-20}$alkyl, p) —S(O)$_m$—OC$_{1-20}$alkyl, q) a C$_{1-20}$alkyl group, r) a C$_{2-20}$alkenyl group, s) a C$_{2-20}$alkynyl group, t) a C$_{1-20}$alkoxy group, u) a C$_{3-14}$cycloalkyl group, v) a C$_{6-14}$aryl group, w) a 3-14 membered cycloheteroalkyl group, or x) a 5-14 membered heteroaryl group, wherein each of the C$_{1-20}$alkyl groups, the C$_{2-20}$alkenyl group, the C$_{2-20}$alkynyl group, the C$_{3-14}$cycloalkyl group, the C$_{6-14}$aryl group, the 3-14 membered cycloheteroalkyl group, and the 5-14 membered heteroaryl group optionally is substituted with 1-4 $R^i$ groups;

$R^i$, at each occurrence, is a) halogen, b) —CN, c) —NO$_2$, d) oxo, e) —OH, f) —NH$_2$, g) —NH(C$_{1-20}$alkyl), h) —N(C$_{1-20}$alkyl)$_2$, i) —N(C$_{1-20}$alkyl)-C$_{6-14}$aryl, j) —N(C$_{6-14}$aryl)$_2$, k) —S(O)$_m$H, l) —S(O)$_m$—C$_{1-20}$alkyl, m) —S(O)$_2$OH, n) —S(O)$_m$—OC$_{1-20}$alkyl, o) —S(O)$_m$—OC$_{6-14}$aryl, p) —CHO, q) —C(O)—C$_{1-20}$alkyl, r) —C(O)—C$_{6-14}$aryl, s) —C(O)OH, t) —C(O)—OC$_{1-20}$alkyl, u) —C(O)—OC$_{6-14}$aryl, v) —C(O)NH$_2$, w) —C(O)NH—C$_{1-20}$alkyl, x) —C(O)N(C$_{1-20}$alkyl)$_2$, y) —C(O)NH—C$_{6-14}$aryl, z) —C(O)N(C$_{1-20}$alkyl)-C$_{6-14}$ aryl, aa) —C(O)N(C$_{6-14}$aryl)$_2$, ab) —C(S)NH$_2$, ac) —C(S)NH—C$_{1-20}$alkyl, ad) —C(S)N(C$_{1-20}$alkyl)$_2$, ae) —C(S)N(C$_{6-14}$aryl)$_2$, af) —C(S)N(C$_{1-20}$alkyl)-C$_{6-14}$aryl, ag) —C(S)NH—C$_{6-14}$aryl, ah) —S(O)$_m$NH$_2$, ai) —S(O)$_m$NH(C$_{1-20}$alkyl), aj) —S(O)$_m$ N(C$_{1-20}$alkyl)-, ak) —S(O)$_m$NH(C$_{6-14}$aryl), al) —S(O)$_m$ N(C$_{1-20}$alkyl)-C$_{6-14}$aryl, am) —S(O)$_m$N(C$_{6-14}$aryl)$_2$, an) —SiH₃, ao) —SiH(C₁₋₂₀alkyl)₂, ap) —SiH₂(C₁₋₂₀ alkyl), ar) —Si(C₁₋₂₀alkyl)₃, as) a C₁₋₂₀ alkyl group, at) a C₂₋₂₀alkenyl group, au) a C₂₋₂₀alkynyl group, av) a C₁₋₂₀alkoxy group, aw) a C₁₋₂₀alkylthio group, ax) a C₁₋₂₀haloalkyl group, ay) a C₃₋₁₄cycloalkyl group, az) a C₆₋₁₄aryl group, ba) a 3-14 membered cycloheteroalkyl group, or bb) a 5-14 membered heteroaryl group;

Y, at each occurrence, is a) a divalent C₁₋₂₀alkyl group, b) a divalent C₁₋₂₀haloalkyl group, or c) a covalent bond;

m, at each occurrence, is 0, 1, or 2; and q, at each occurrence, is an integer in the range of 1 to 20.

In various embodiments, each of πc-1 and π-1' can be a perylene moiety optionally substituted with 1-8 R$^a$ groups, wherein R$^a$ is as defined herein. In some embodiments, one or more CH or CR$^a$ groups of the perylene moiety can be replaced by a heteroatom such as SiH, SiR$^a$, N, or P, wherein R$^a$ is as defined herein. For example, each of π-1 and π-1' can be a perylene moiety optionally and independently substituted with 1-8 electron-withdrawing groups, examples of which include F, Cl, Br, and CN. In other embodiments, π-1 and/or π-1' can be a fused ring moiety independently selected from a perylene moiety, a naphthalene moiety, a coronene moiety, and an anthracene moiety, each of which optionally and independently can be substituted with 1-8 R$^a$ groups and/or optionally and independently can include one or more CH or CR$^a$ groups that are replaced by a heteroatom such as SiH, SiR$^a$, N, or P, wherein R$^a$ is as defined herein.

In certain embodiments, Q and Q' independently can be:

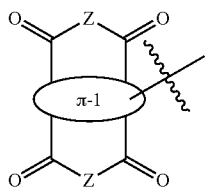

wherein π-1 is:

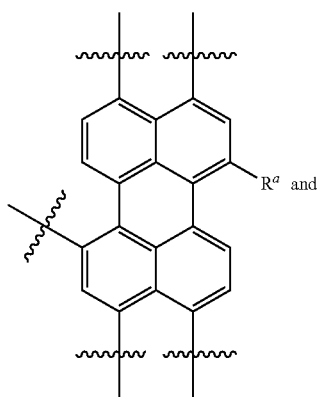

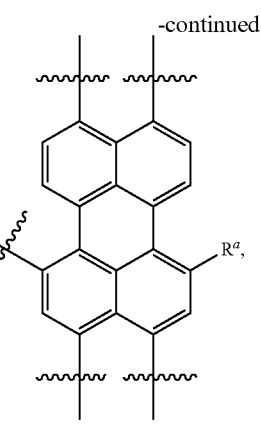

wherein Z and R$^a$ are as defined herein.

In various embodiments, Q and Q' can be an anhydride (i.e., Z is O) or an imide (i.e., Z is NR$^b$). In embodiments where Q and Q' are imides, R$^b$ can be H or a substitution groups where the substitution group can impart improved desirable properties to the compound as a whole. For example, certain substitution groups including one or more electron-withdrawing or electron-donating moieties can modulate the electronic properties of the compound, while substitution groups that include one or more aliphatic chains can improve the solubility of the compound in organic solvents. Accordingly, in various embodiments, R$^b$ can be selected from H, —(CH₂CH₂O)$_q$H, —(CH₂CH₂O)$_q$—CH₃, —C(O)R$^g$, —C(O)NR$^g$R$^h$, —S(O)$_m$R$^g$, a C₁₋₂₀alkyl group, a C₂₋₂₀alkenyl group a C₂₋₂₀alkynyl group a C₁₋₂₀alkoxy group, a —Y—C₃₋₁₄cycloalkyl group, a —Y—C₆₋₁₄aryl group, a —Y-3-14 membered cycloheteroalkyl group, or a —Y-5-14 membered heteroaryl group, where each of the C₁₋₂₀alkyl group, the C₂₋₂₀alkenyl group, the C₂₋₂₀alkynyl group, the C₁₋₂₀alkoxy group, the C₃₋₁₄cycloalkyl group, the C₆₋₁₄aryl group, the 3-14 membered cycloheteroalkyl group, and the 5-14 membered heteroaryl group optionally can be substituted with 1-4 R$^i$ groups, where m, q, R$^g$, R$^h$, R$^i$, and Y are as defined herein. In some embodiments, R$^b$, at each occurrence, can be H, —(CH₂CH₂O)$_q$H, —(CH₂CH₂O)$_q$—CH₃, —C(O)R$^g$, —C(O)NR$^g$R$^h$, or —S(O)$_m$R$^g$, where m, q, R$^g$ and R$^h$ are as defined herein. In some embodiments, R$^b$, at each occourrence, can be selected from a C₁₋₂₀alkyl group, a C₂₋₂₀alkenyl group, a C₂₋₂₀alkynyl group, a —Y—C₃₋₁₄cycloalkyl group, a —Y—C₆₋₁₄aryl group, a —Y-3-14 membered cycloheteroalkyl group, and a —Y-5-14 membered heteroaryl grouop, where each of the C₁₋₂₀alkyl group, the C₂₋₂₀alkenyl group, the C₂₋₂₀alkynyl group, the C₃₋₁₄cycloalkyl group, the C₆₋₁₄aryl group, the 3-14 membered cycloheteroalkyl group, and the 5-14 membered heteroaryl group optionally can be substituted with 1-4 R$^i$ groups, where Y and R$^i$ are as defined herein. In certain embodiments, R$^b$, at each occurrence, can be selected from a C₁₋₂₀alkyl group, a C₂₋₂₀alkenyl group, and a C₂₋₂₀alkynyl group, where each of the C₁₋₂₀alkyl group, the C₂₋₂₀alkenyl group, and the C₂₋₂₀alkynyl group optionally can be substituted with 1-4 R$^i$ groups, where R$^i$ is as defined herein. For example, R$^b$, at each occurrence, can be a C₁₋₂₀alkyl group optionally substituted with 1-4 R$^i$ groups, where R$^i$ is as defined herein. In particular embodiments, R$^b$, at each occurrence, can be a methyl group, and ethyl group, a linear or branched propyl group, a linear or branched butyl group, a linear or branched pentyl group, a linear or branched hexyl group, a linear or branched heptyl group, or a linear or branched octyl group. For example, R$^b$, at each occurrence, can be a hexyl group (including a methylpentyl group and the like), a heptyl group, or an octyl group (including an ethylhexyl group and the like).

In various embodiments, L is a linker comprising 1-6 optionally substituted $C_{6-22}$aryl or 5-22 membered heteroaryl groups, wherein each group can be identical or different. In various embodiments, L can be selected from a) —$(Ar^1)_n$—, b) —$(Ar^2)_n$—, c) —$(Ar^1)_n$—$(Ar^2)_{n'}$—$(Ar^1)_{n''}$—, and d) —$(Ar^2)_n$—$(Ar^1)_{n'}$—$(Ar^2)_{n''}$—,
wherein:
  $Ar^1$, at each occurrence, independently is a 5- or 6-membered aryl or heteroaryl group, each optionally substituted with 1-4 $R^i$ groups;
  $Ar^2$, at each occurrence, independently is a polycyclic 8-22 membered aryl or heteroaryl group, each optionally substituted with 1-12 $R^i$ groups;
  n, n', and n'' independently are 1, 2, 3, 4, 5, 6; and
  $R^i$ is as defined herein.

In some embodiments, $Ar^1$, at each occurrence, independently can be selected from:

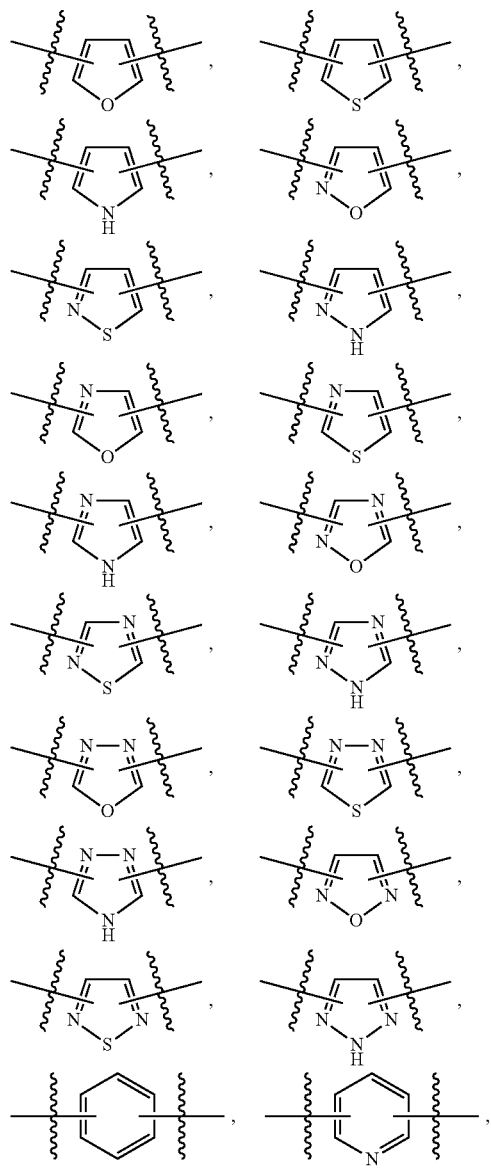

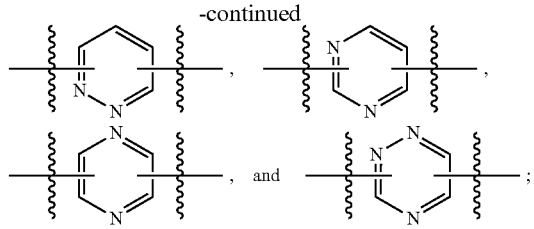

each of which optionally can be substituted with 1-4 $R^i$ groups, wherein $R^i$ is as defined herein. For example, $Ar^1$, at each occurrence, independently can be selected from a phenyl group, a thienyl group, a furyl group, a pyrrolyl group, an isothiazolyl group, a thiazolyl group, a 1,2,4-thiadiazolyl group, a 1,3,4-thiadiazolyl group, and a 1,2,5-thiadiazolyl group, wherein each of these groups optionally can be substituted with 1-4 substituents independently selected from a halogen, —CN, an oxo group, a $C_{1-6}$ alkyl group, a $C_{1-6}$alkoxy group, a $C_{1-6}$haloalkyl group, $NH_2$, $NH(C_{1-6}$alkyl) and $N(C_{1-6}$alkyl$)_2$. In particular embodiments, $Ar^1$, at each occurrence, independently can be selected from a thienyl group, an isothiazolyl group, a thiazolyl group, a 1,2,4-thiadiazolyl group, a 1,3,4-thiadiazolyl group, a 1,2,5-thiadiazolyl group, a phenyl group, and a pyrrolyl group, wherein each of these groups optionally can be substituted with 1-2 substituents independently selected from a halogen, —CN, an oxo group, a $C_{1-6}$ alkyl group, a $C_{1-6}$alkoxy group, a $C_{1-6}$haloalkyl group, $NH_2$, $NH(C_{1-6}$alkyl) and $N(C_{1-6}$alkyl$)_2$. In some embodiments, one or more $Ar^1$ groups can be unsubstituted. In some embodiments, —$(Ar^1)_n$— and —$(Ar^1)_{n''}$— can include one or more thienyl groups, isothiazolyl groups, thiazolyl groups, 1,2,4-thiadiazolyl groups, 1,3,4-thiadiazolyl groups, and/or 1,2,5-thiadiazolyl groups, wherein each of these groups optionally can be substituted with 1-2 $C_{1-6}$alkyl groups.

In some embodiments, $Ar^2$, at each occurrence, independently can be selected from an optionally substituted polycyclic 8-22 membered aryl or heteroaryl group comprising one or more phenyl, thienyl, or thiazolyl groups fused to a moiety selected from:

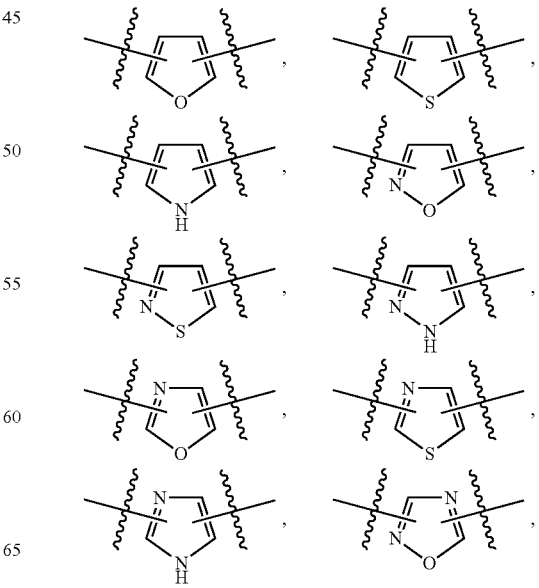

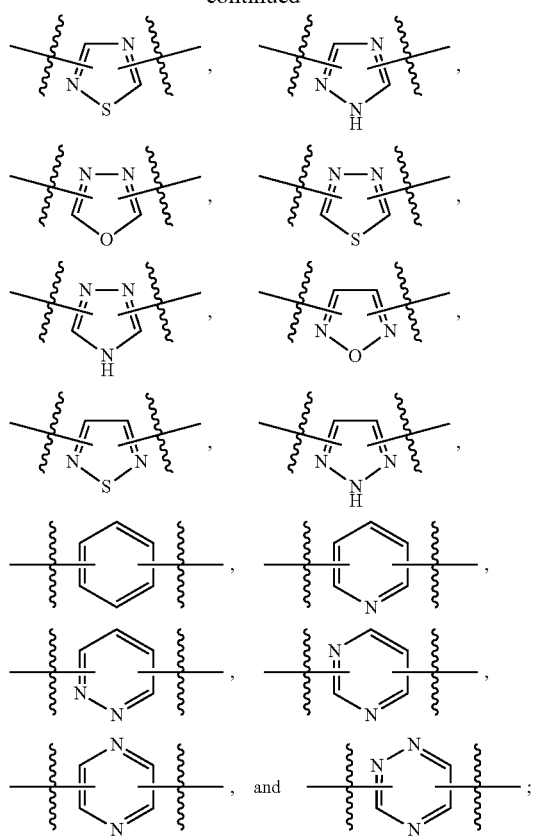
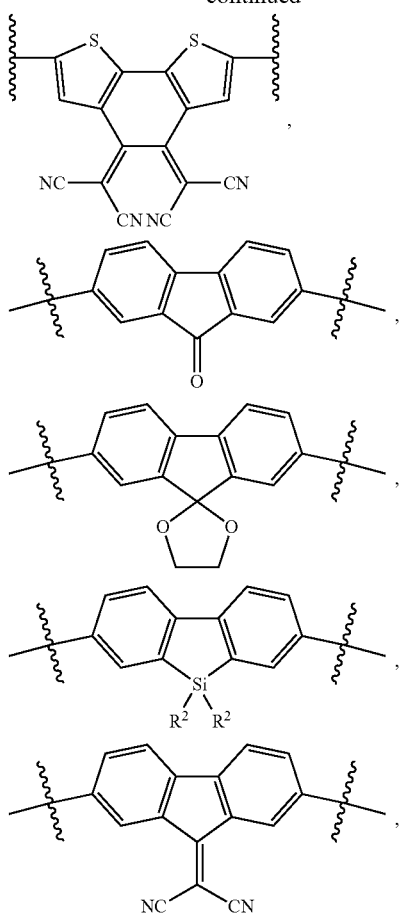
For example, Ar² can be selected from:
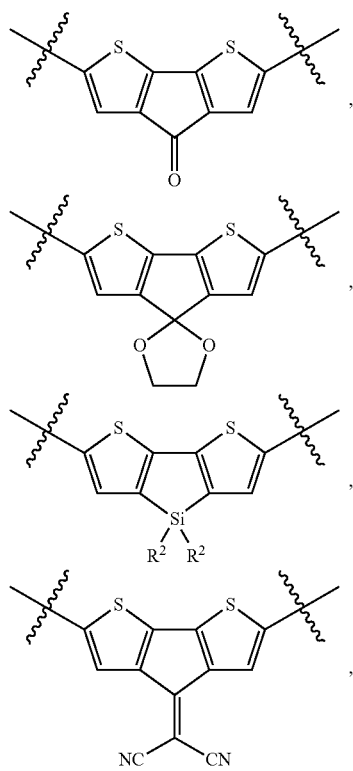

-continued
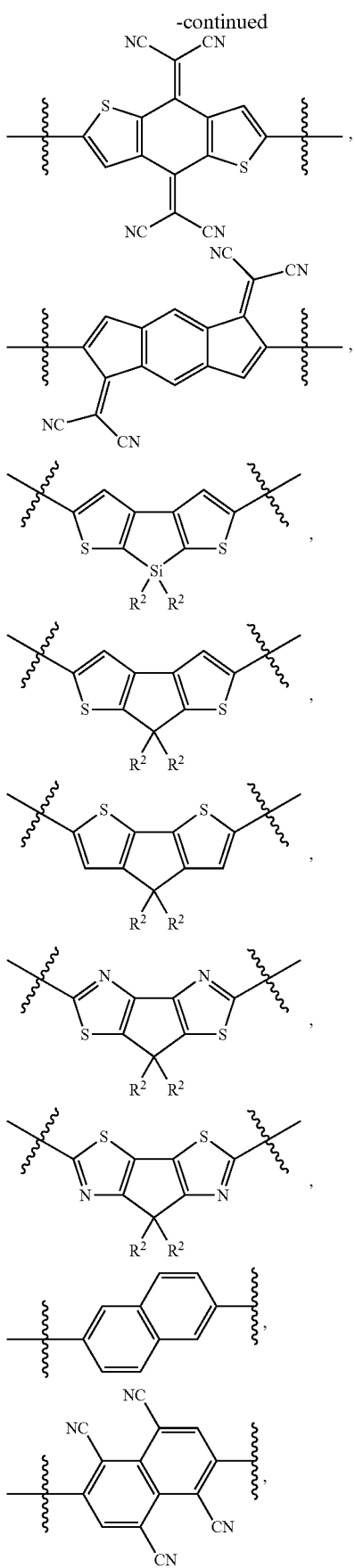
-continued
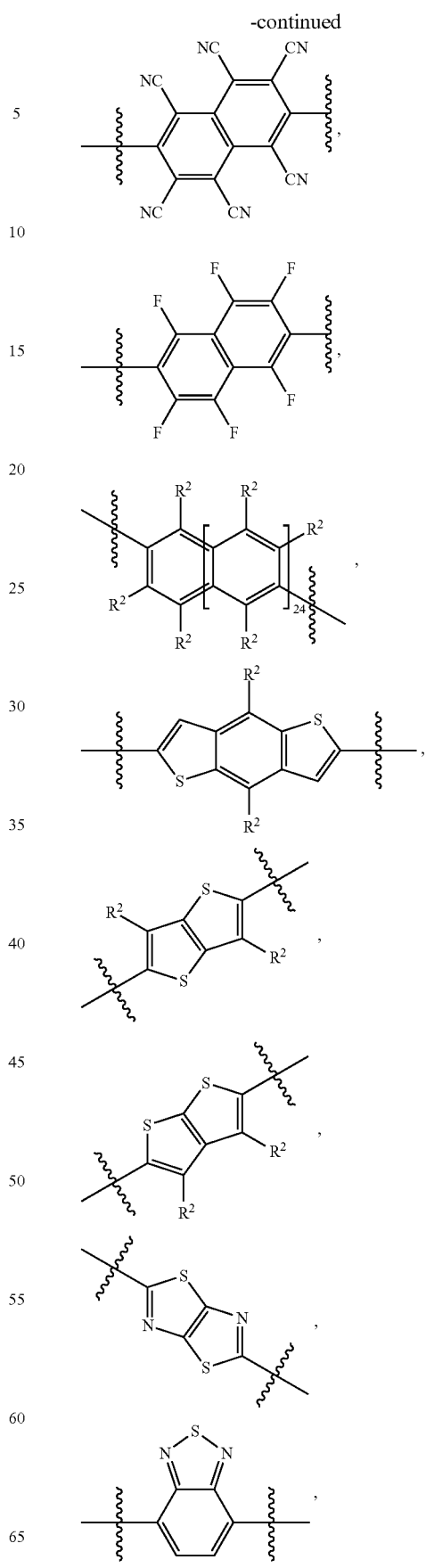

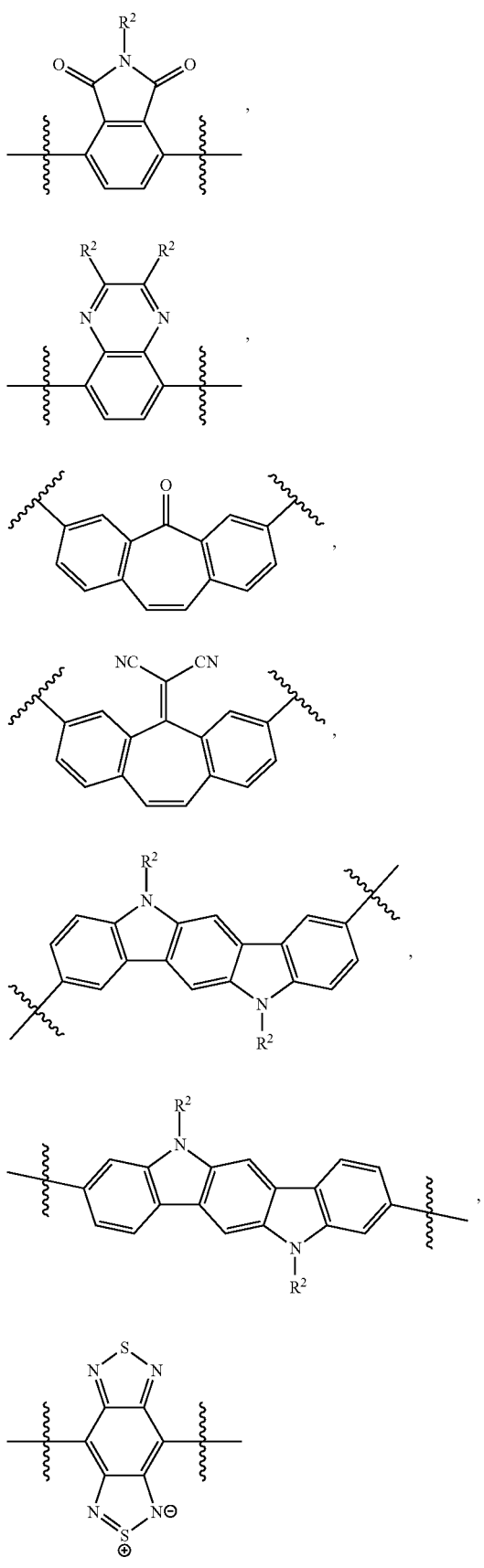
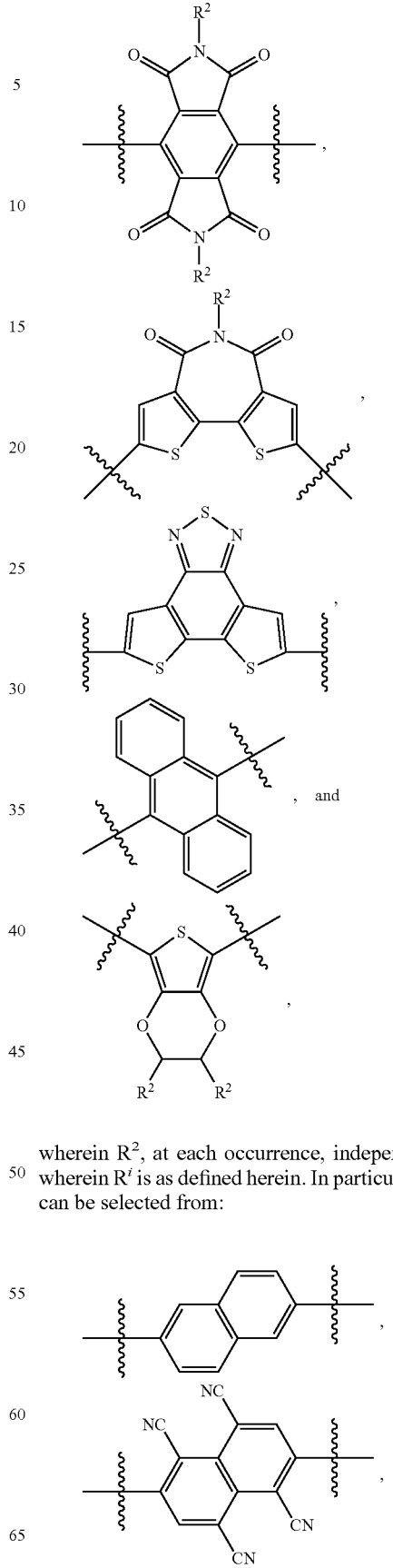
wherein $R^2$, at each occurrence, independently is H or $R^i$, wherein $R^i$ is as defined herein. In particular embodiments, L can be selected from:
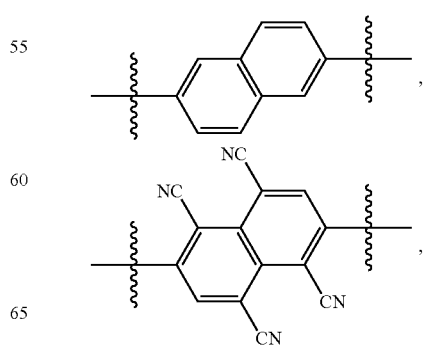

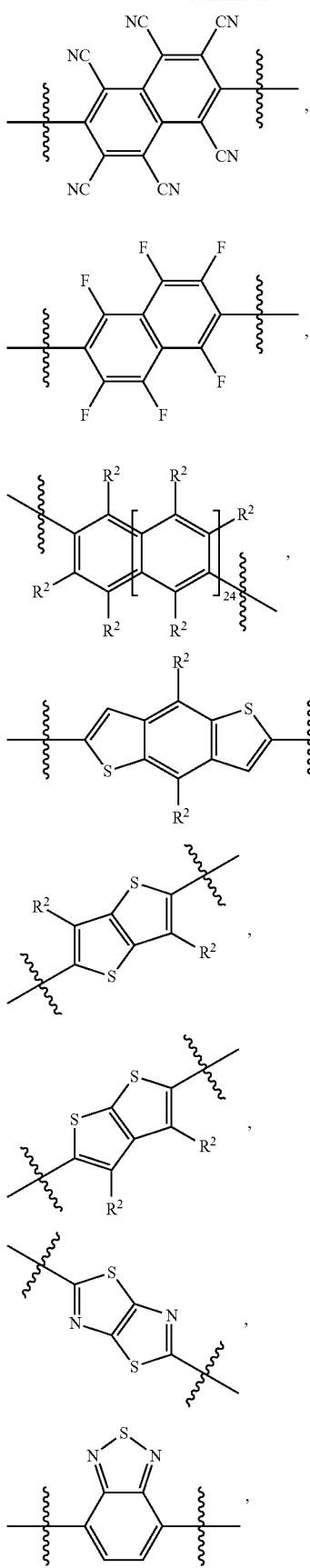
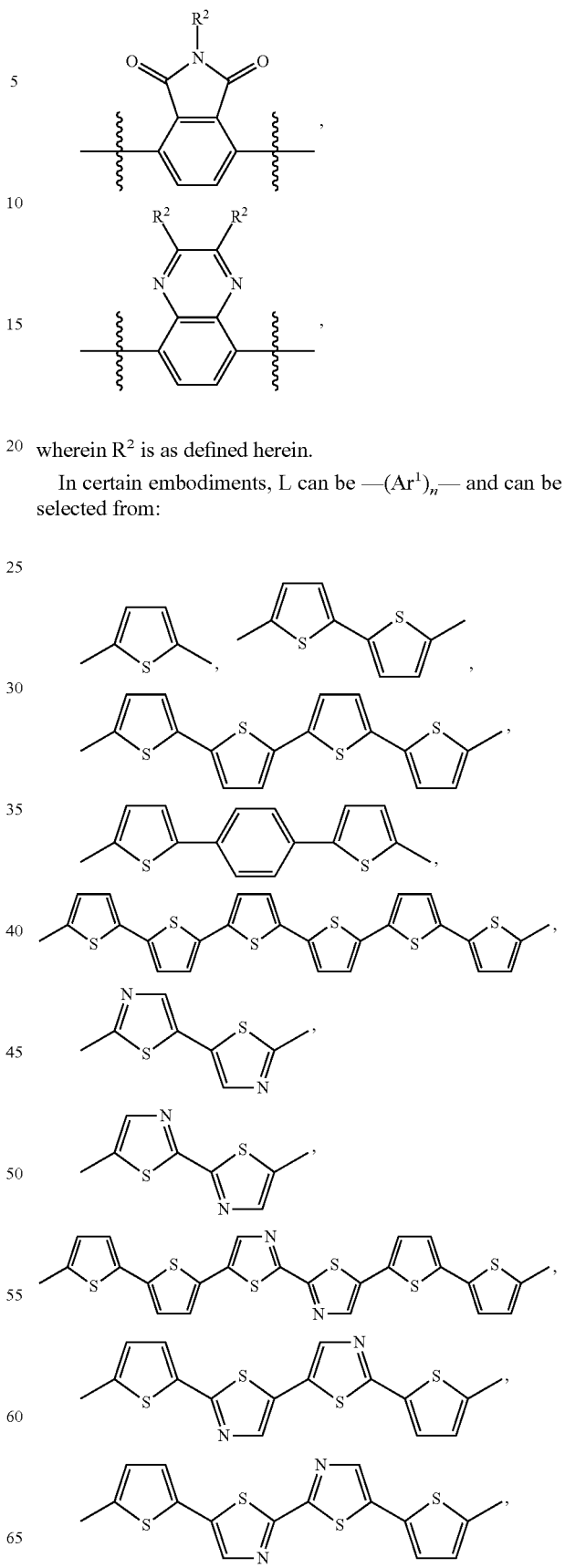
wherein $R^2$ is as defined herein.
In certain embodiments, L can be —$(Ar^1)_n$— and can be selected from:

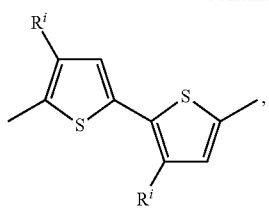
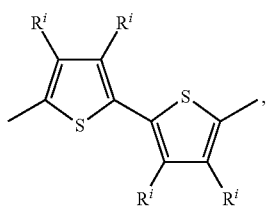
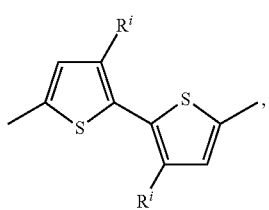
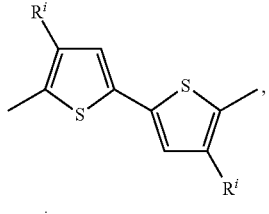
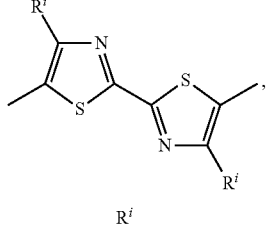
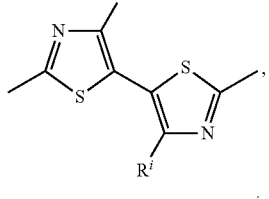
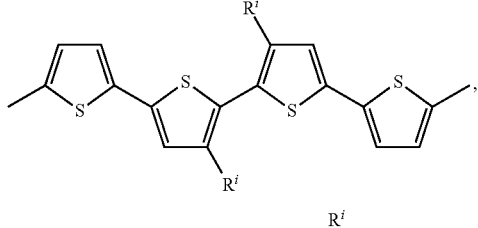
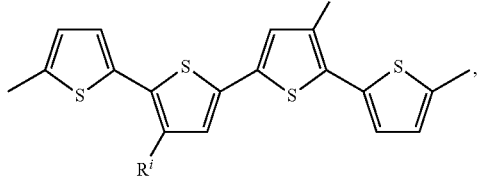
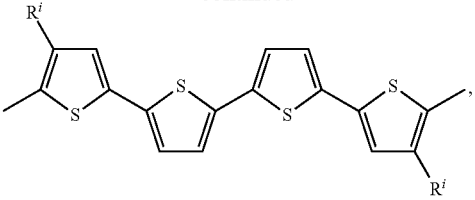
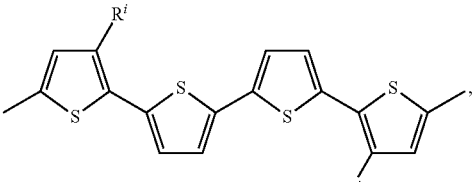
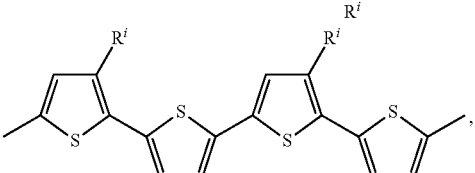
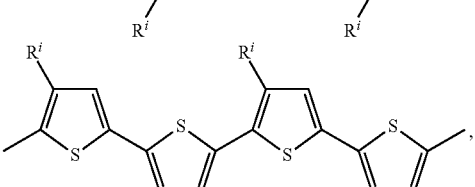
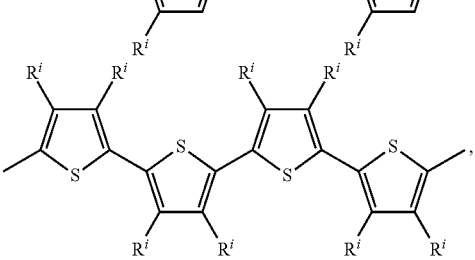
wherein $R^i$ is as defined herein.
In certain embodiments, L can be —(Ar$^2$)—, wherein Ar$^2$ is as defined herein. For example, L can be selected from:
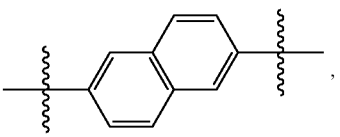
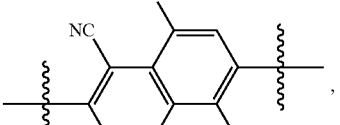
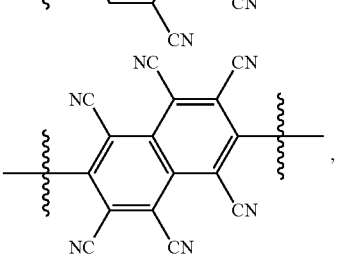

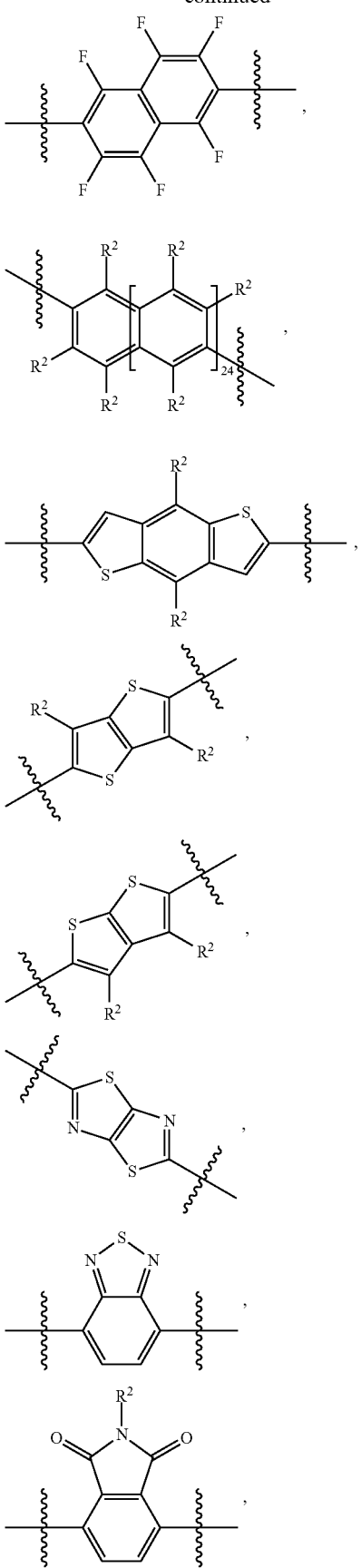

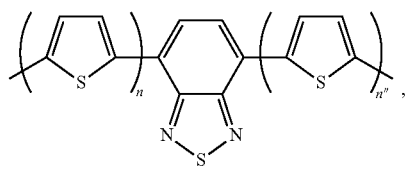

wherein R² is as defined herein.

In certain embodiments, L can be —(Ar¹)$_n$—(Ar²)—(Ar¹)$_{n''}$—, wherein Ar¹, Ar², n, and n'' are as defined herein. For example, L can be wherein each of n and n'' is 1 or 2.

In some embodiments, L can be a linker represented by A-B-A' or B-A-B', wherein:

A and A' independently are selected from a) a divalent $C_{1-20}$alkyl group, b) a divalent $C_{2-20}$alkenyl group, c) a divalent $C_{2-20}$alkynyl group, d) a divalent $C_{1-20}$haloalkyl group, e) a divalent $C_{1-20}$alkoxy group, and f) a covalent bond, wherein each of a)-e) optionally is substituted with 1-4 $R^i$ groups;

B and B' independently are selected from a) —O—, b) —S—, c) —NR$^e$—, d) —C(O)—, e) —C(O)O—, f) —OC(O)—, g) —C(O)NR$^e$—, h) —NR$^e$C(O)—, i) a divalent $C_{3-14}$cycloalkyl group, j) a divalent $C_{6-14}$aryl group, k) a divalent 3-14 membered cycloheteroalkyl group, l) a divalent 5-14 heteroaryl group, and m) a covalent bond, wherein each of i)-l) optionally is substituted with 1-4 $R^i$ groups;

wherein R$^e$ is a) H, b) a $C_{1-6}$alkyl group, c) a $C_{6-14}$aryl group, or d) a —$C_{1-6}$alkyl-$C_{6-14}$aryl group, wherein each of the $C_{1-6}$alkyl groups and the $C_{6-14}$aryl groups optionally is substituted with 1-4 $R^i$ groups; and $R^i$ is as defined herein.

In certain embodiments, B and B' independently can be selected from —O—, —S—, —NR$^e$—, —C(O)—, —C(O)O—, —OC(O)—, —C(O)NR$^e$—, —NR$^e$C(O)—, and a covalent bond, where R$^e$ is as defined herein. In various embodiments, B and B' independently can be selected from a divalent $C_{3-14}$ cycloalkyl group, a divalent $C_{6-14}$aryl group, a divalent 3-14 membered cycloheteroalkyl group, and a divalent 5-14 heteroaryl group, where each of the divalent $C_{3-14}$cycloalkyl group, the divalent $C_{6-14}$ aryl group, the divalent 3-14 membered cycloheteroalkyl group, and the divalent 5-14 heteroaryl group optionally can be substituted with 1-4 $R^i$ groups where $R^i$ is as defined herein. In some embodiments, B and B' independently can be selected from a divalent $C_{6-14}$aryl group, a divalent 5-14 heteroaryl group, and a covalent bond, where each of the divalent $C_{6-14}$aryl group and the divalent 5-14 heteroaryl group optionally can be substituted with 1-4 $R^i$ groups, where $R^i$ is as defined herein. For example, in the embodiments where B and B' independently are selected from a divalent $C_{6-14}$aryl group and a divalent 5-14 heteroaryl group, the divalent $C_{6-14}$aryl group and the divalent 5-14 heteroaryl group independently can be selected from:

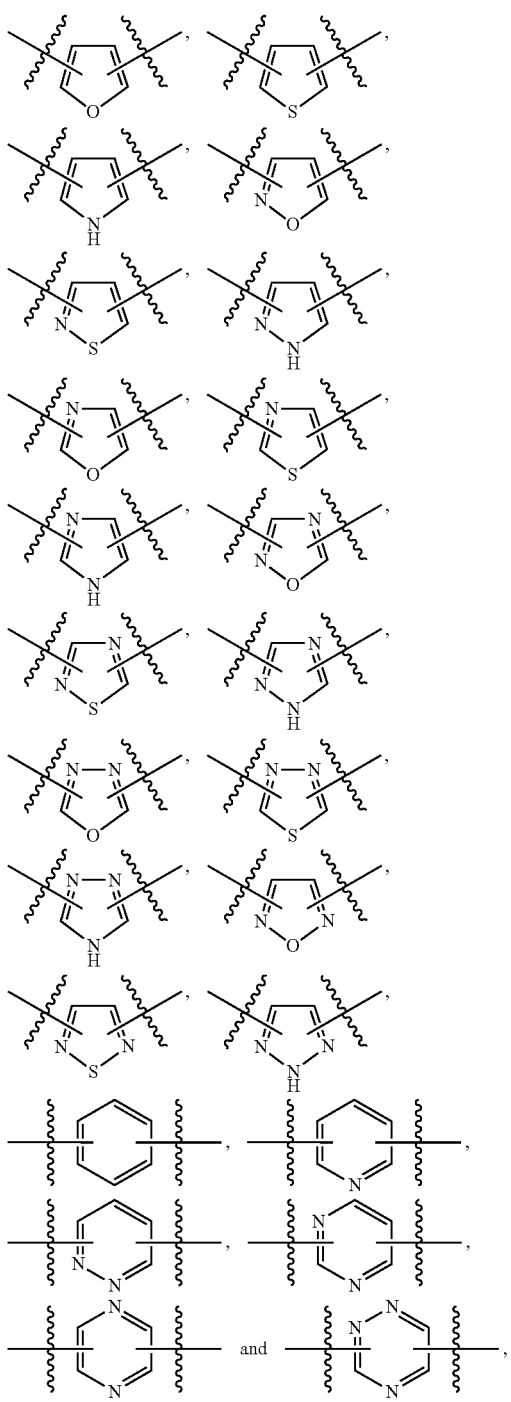

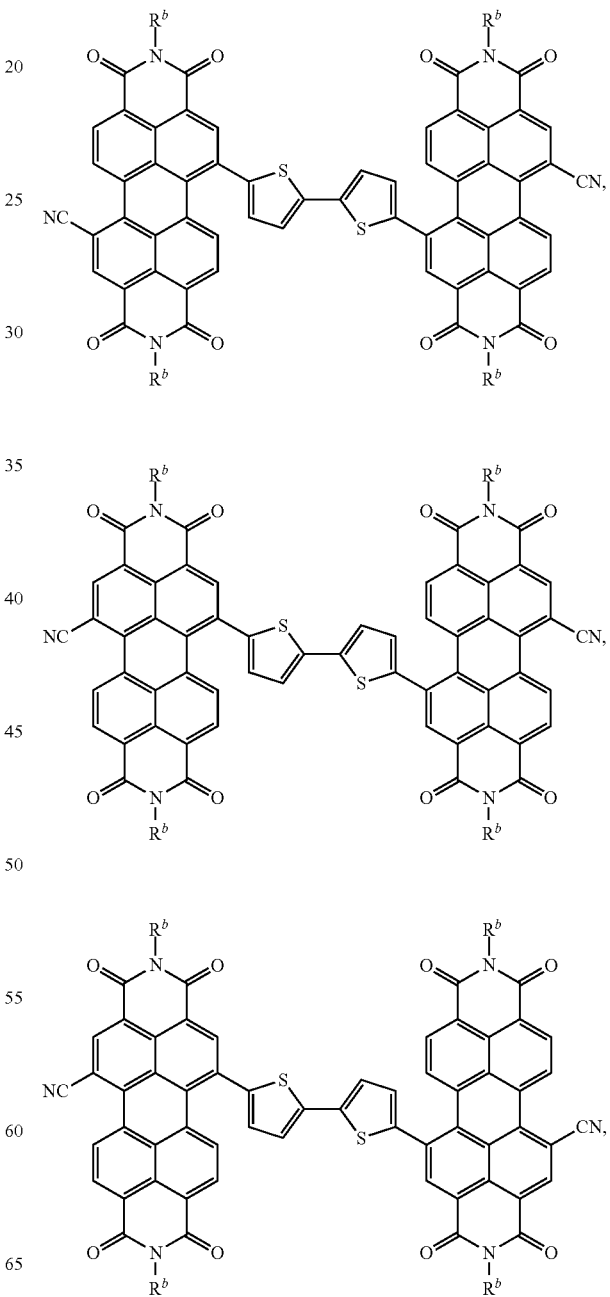

where each of these groups optionally can be fused to a $C_{6-14}$ aryl group or a 5-14 membered heteroaryl group, including a phenyl group or a five or six-membered heteroaryl group. In certain embodiments, B and B' independently can be selected from a thienyl group, a furanyl group, a pyrrolyl group, a phenyl group, a pyridyl group, an isothiazolyl group, a thiadiazolyl group, a benzothienyl group, a benzoisothiazolyl group, a benzothiadiazolyl group, and an indolyl group, each of which optionally can be substituted with 1-4 $R^i$ groups, where $R^i$ is as defined herein.

In some embodiments, the compounds of the present teachings can be symmetrical. In some embodiments, the compounds of the present teachings can be asymmetrical. Without being bound to any specific theory, it is believed that the symmetry of certain compounds can facilitate crystallization of such compounds. The modulation of the symmetry of such compounds, therefore, may be used to tune the electronic properties of the resulting semiconductor materials. Accordingly, in certain embodiments, the compounds of the present teachings can be crystalline. In certain embodiments, the present teachings can provide semiconductor materials with tunable electronic properties. For example, the electronic properties of such semiconductor materials can be changed in a continuous manner or in a step-wise manner.

In particular embodiments, the compounds of the present teachings can have the formula:

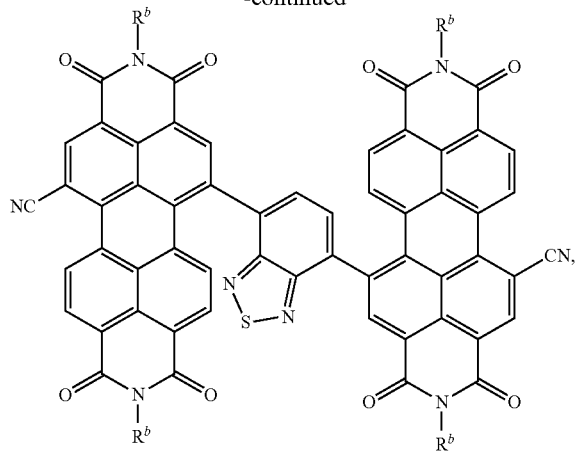
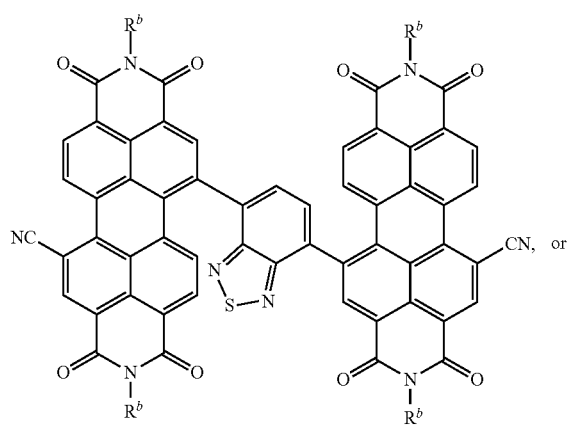
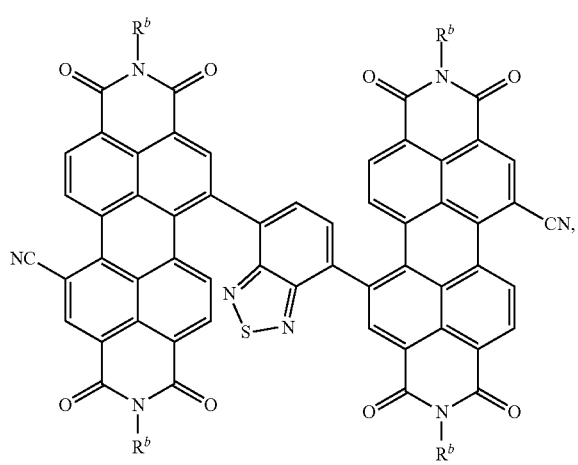

wherein $R^b$ is as defined herein. For example, $R^b$ can be a linear (straight chain) or branched $C_{4-20}$ alkyl group such as an n-octyl group, an ethylhexyl (e.g., 2-ethylhexyl) group, or a methylpentyl (e.g., 1-methylp entyl) group.

In another aspect, the present teachings provide methods of preparing compounds of Formula I. In various embodiments, the method can include subjecting compounds of Formula II or Formula III, or both:

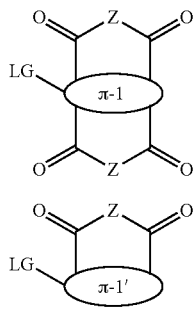

to coupling reactions,
wherein:
LG is a leaving group; and
π-1, π-1', and Z are as defined herein.

In some embodiments, LG, at each occurrence, can be a halogen or azide. In certain embodiments, LG, at each occurrence, can be a halogen, including Cl, Br, or I. In particular embodiments, LG, at each occurrence, can be Br. Accordingly, for example, the compounds of Formula II or Formula III independently can be selected from:

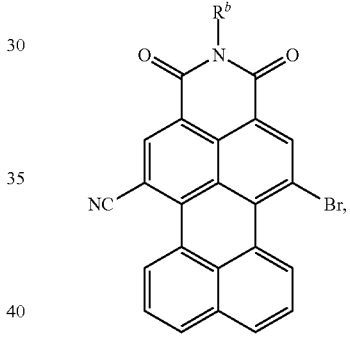
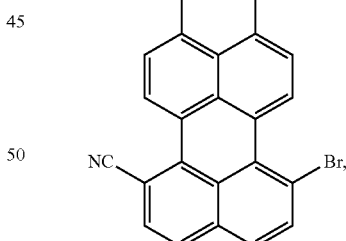
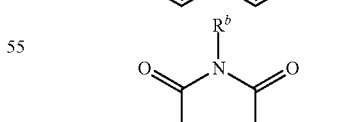
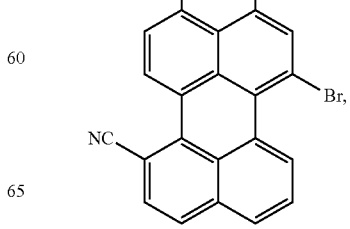

-continued

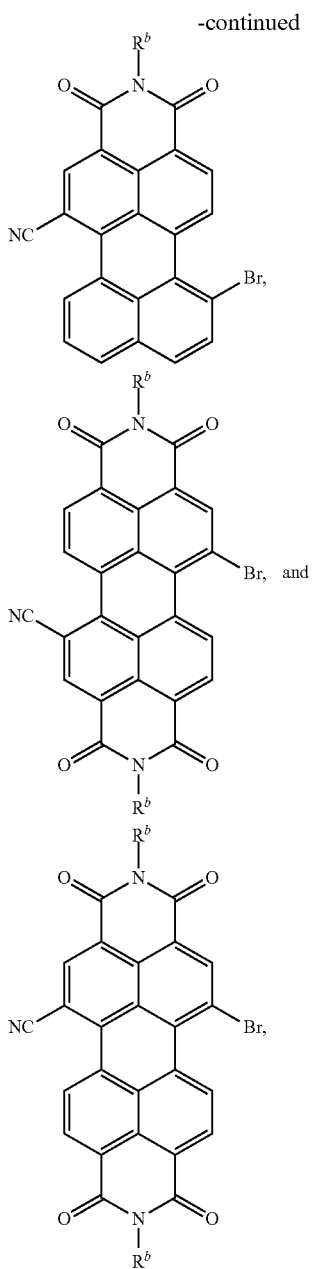

where R$^b$ is as defined herein.

Figure 2:
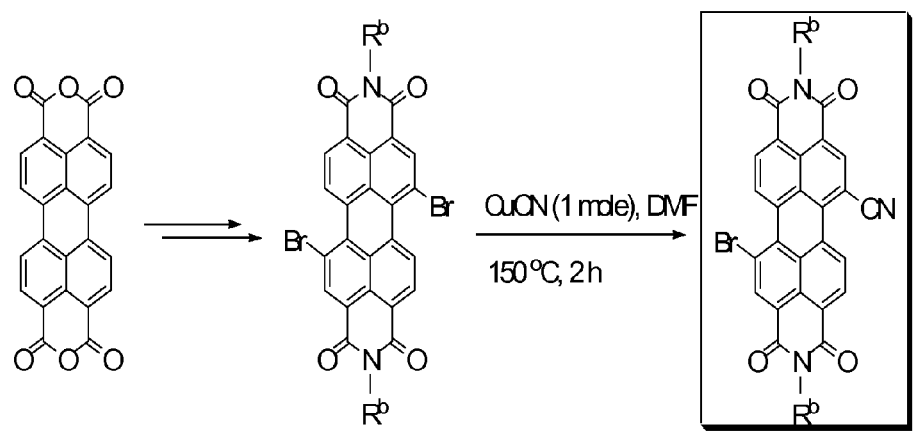
FIG. 2 shows an exemplary method of preparing certain compounds of the present teachings, for example, PDI-BrCNs.
Figure 3:
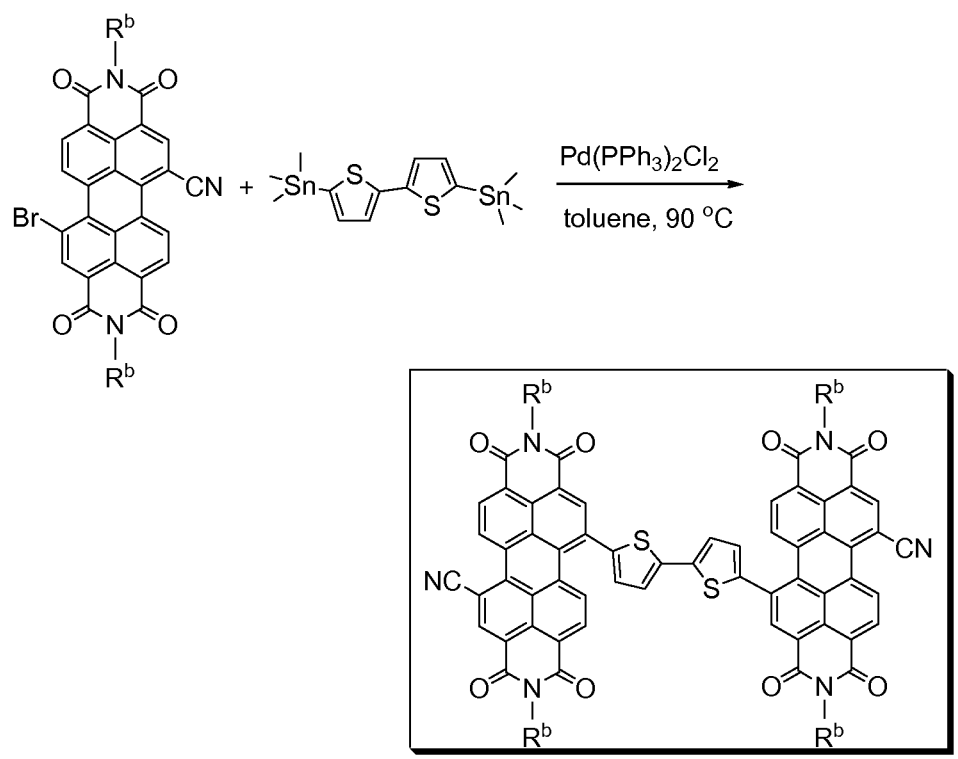
FIG. 3 shows an exemplary method of preparing certain compounds of the present teachings, for example, BPDI-BTs.
Figure 4:
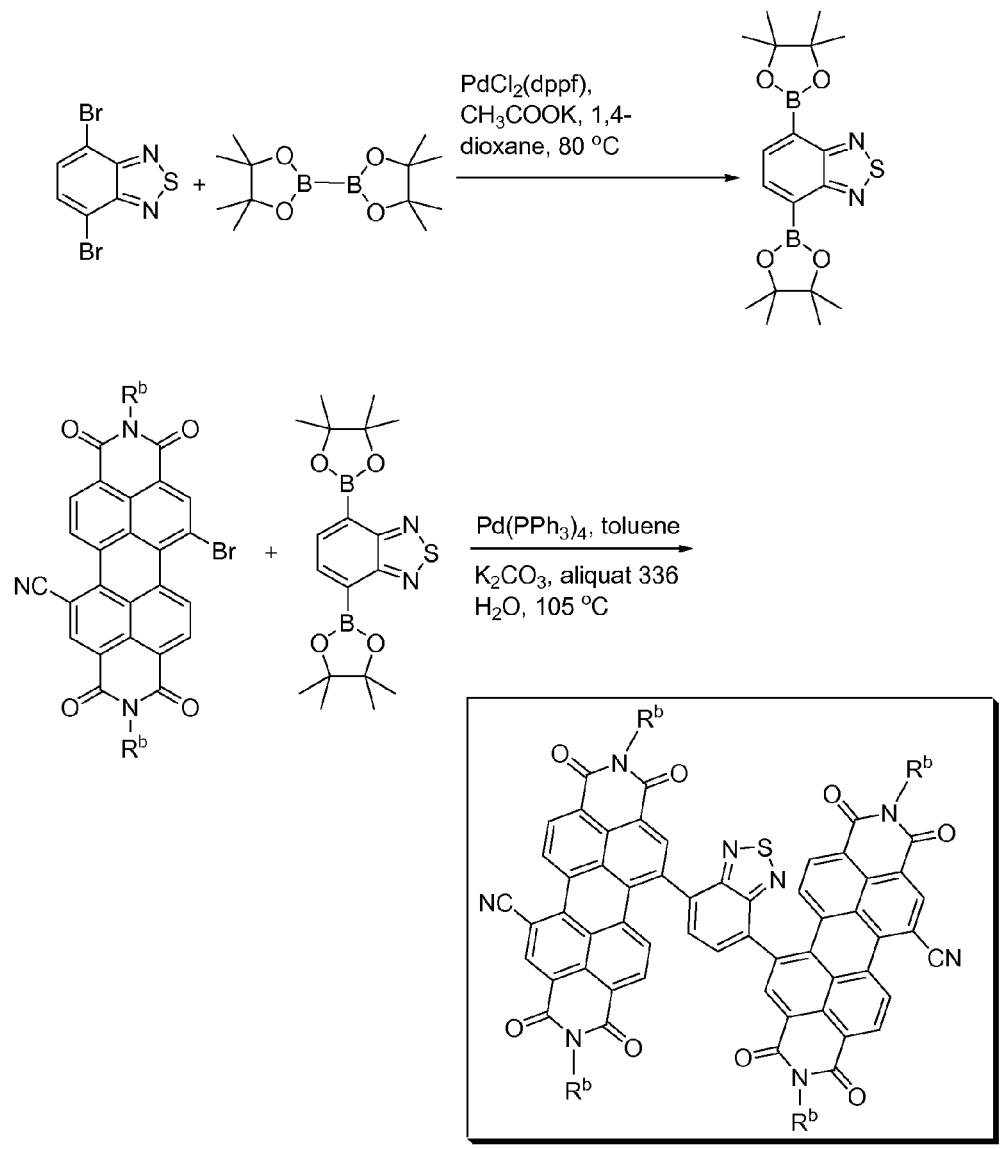
FIG. 4 shows an exemplary method of preparing an embodiment of the present teachings, for example, BPDI-BTZ.

Compounds of the present teachings can be prepared in accordance with the procedures outlined in FIG. 1, for example, using reaction described in FIGS. 3 and 4, from compounds prepared according to procedures analogous to those described in FIG. 2, or from commercially available starting materials, compounds known in the literature, or via other readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (NMR, e.g., $^1$H or $^{13}$C), infrared spectroscopy (IR), spectrophotometry (e.g., UV-visible), mass spectrometry (MS), or by chromatography such as high pressure liquid chromatograpy (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Compounds of Formula I can be prepared generally according to the general scheme shown in FIG. 1. As shown, polycyclic compounds including leaving group X, i.e., Q-X and/or Q'-X, can be subject to a coupling reaction with a precursor of linker L, i.e., Y-L-Y, where each Y is a leaving group, to provide compounds of the present teachings. A "coupling" or "coupling reaction" as used herein refers to a chemical reaction in which two or more molecules react to form one new molecule. In some embodiments, the coupling reaction can take place in the absence of catalyst. In some embodiments, the coupling reaction can be facilitated by one or more catalysts. Examples of coupling reactions can include Castro-Stephens coupling, Kumada coupling, Heck coupling, Sonogashira coupling, Negishi coupling, Stille coupling, Suzuki coupling, Hiyama coupling, Buchard coupling, Fukuyama coupling, and the like. The chemistry of the above name reactions is discussed in Metal-Catalyzed Cross-Coupling Reactions (F. Diederich et al. eds., Wiley-VCH, Weinheim, 1998), the entire disclosure of which is incorporated by reference herein for all purposes.

Compounds of the present teachings can be used to prepare semiconductor materials (e.g., compositions and composites), which in turn can be used to fabricate various articles of manufacture, structures, and devices. In some embodiments, semiconductor materials incorporating one or more compounds of the present teachings can exhibit n-type semiconductor activity.

As certain embodiments disclosed herein can be soluble in common solvents and stable under ambient conditions ("ambient stable"), the present teachings can offer processing and operation advantages in the fabrication and/or the use of electrical devices such as thin film semiconductors, field-effect devices, organic light emitting diodes (OLEDs), organic photovoltaics, photodetectors, capacitors, and sensors. As used herein, a compound can be considered soluble in a solvent when at least 0.1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone, and methyl ethyl ketone; ethers such as tetrahydrofuran, dioxane, bis(2-methoxyethyl)

ether, diethyl ether, di-isopropyl ether, and t-butyl methyl ether; alcohols such as methanol, ethanol, butanol, and isopropyl alcohol; aliphatic hydrocarbons such as hexanes; esters such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone.

Various deposition techniques, including various solution processing techniques, have been used with organic electronics. For example, much of the printed electronics technology has focused on inkjet printing, primarily because this technique offers greater control over feature position and multilayer registration. Inkjet printing is a noncontact process, which offers the benefits of not requiring a preformed master (compared to contact printing techniques), as well as digital control of ink ejection, thereby providing drop-on-demand printing. Micro-dispensing is another non-contact method of printing. However, contact printing techniques have the advantage of being well-suited for very fast roll-to-roll processing. Exemplary contact printing techniques include, but are not limited to, screen-printing, gravure printing, offset printing, flexographic printing, lithographic printing, pad printing, and microcontact printing. As used herein, "printing" includes a noncontact process such as inject printing, microdispensing and the like, and a contact process such as screen-printing, gravure printing, offset printing, flexographic printing, lithographic printing, pad printing, microcontact printing and the like. Other solution processing techniques include, for example, spin coating, drop-casting, zone casting, dip coating, blade coating, or spraying.

Various articles of manufacture including electronic devices, optical devices, and optoelectronic devices, such as field effect transistors (e.g., thin film transistors), photovoltaics, organic light emitting diodes (OLEDs), complementary metal oxide semiconductors (CMOSs), complementary inverters, D flip-flops, rectifiers, and ring oscillators, that make use of the compounds disclosed herein also are within the scope of the present teachings as are methods of making the same.

The present teachings, therefore, further provide methods of preparing a semiconductor material. The methods can include preparing a composition that includes one or more compounds disclosed herein dissolved or dispersed in a liquid medium such as a solvent or a mixture of solvents, depositing the composition on a substrate to provide a semiconductor material precursor, and processing (e.g., heating) the semiconductor precursor to provide a semiconductor material (e.g., a thin film semiconductor) that includes a compound disclosed herein. In various embodiments, the liquid medium can be an organic solvent, an inorganic solvent such as water, or combinations thereof In some embodiments, the composition can further include one or more additives independently selected from detergents, dispersants, binding agents, compatiblizing agents, curing agents, initiators, humectants, antifoaming agents, wetting agents, pH modifiers, biocides, and bactereriostats. For example, surfactants and/or polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying.

The present teachings further provide articles of manufacture such as the various devices described herein that include a composite having a semiconductor material of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), and self-assembled superlattice/self-assembled nanodielectric (SAS/SAND) materials (e.g., described in Yoon, M-H. et al., PNAS, 102 (13): 4678-4682 (2005), the entire disclosure of which is incorporated by reference herein), as well as hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)). One or more of the composites described herein can be embodied within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Other articles of manufacture in which compounds of the present teachings are useful are photovoltaics or solar cells. Compounds of the present teachings can exhibit broad optical absorption and/or a very positively shifted reduction potential, making them desirable for such applications. Accordingly, the compounds described herein can be used as a n-type semiconductor in a photovoltaic design, which includes an adjacent p-type semiconductor material that forms a p-n junction. The compounds can be in the form of a thin film semiconductor, which can be deposited on a substrate to form a composite. Exploitation of compounds of the present teachings in such devices is within the knowledge of a skilled artisan.

Figure 5:
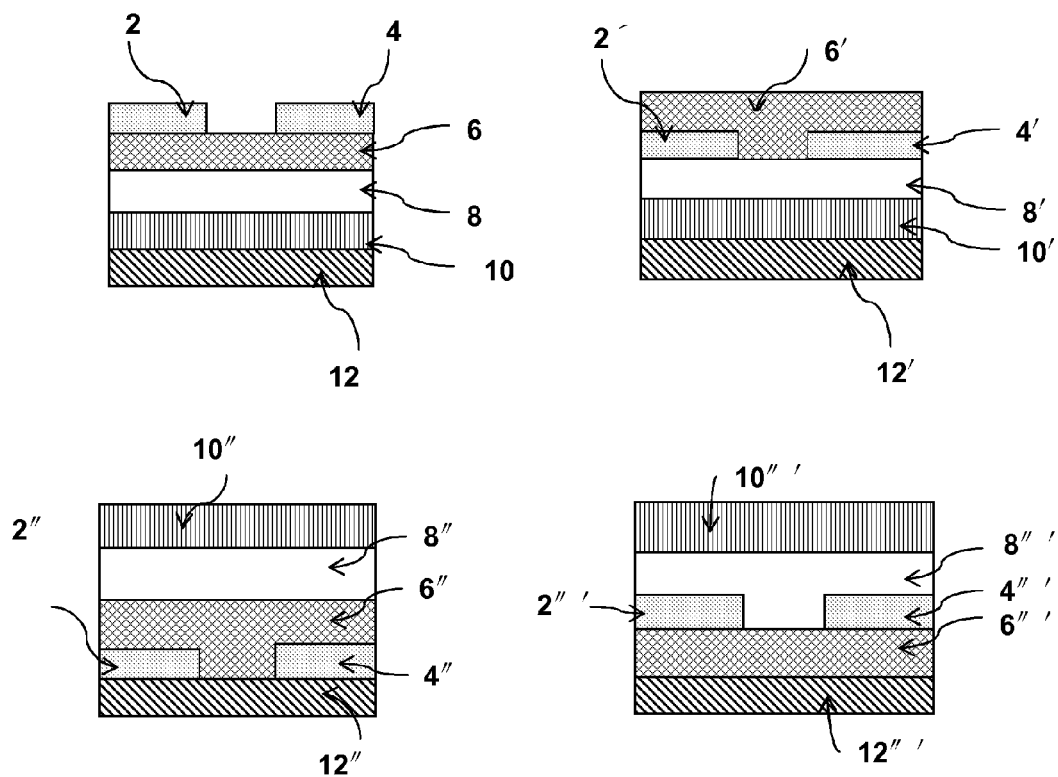
FIG. 5 illustrates different configurations of organic field effect transistors.
Figure 6:
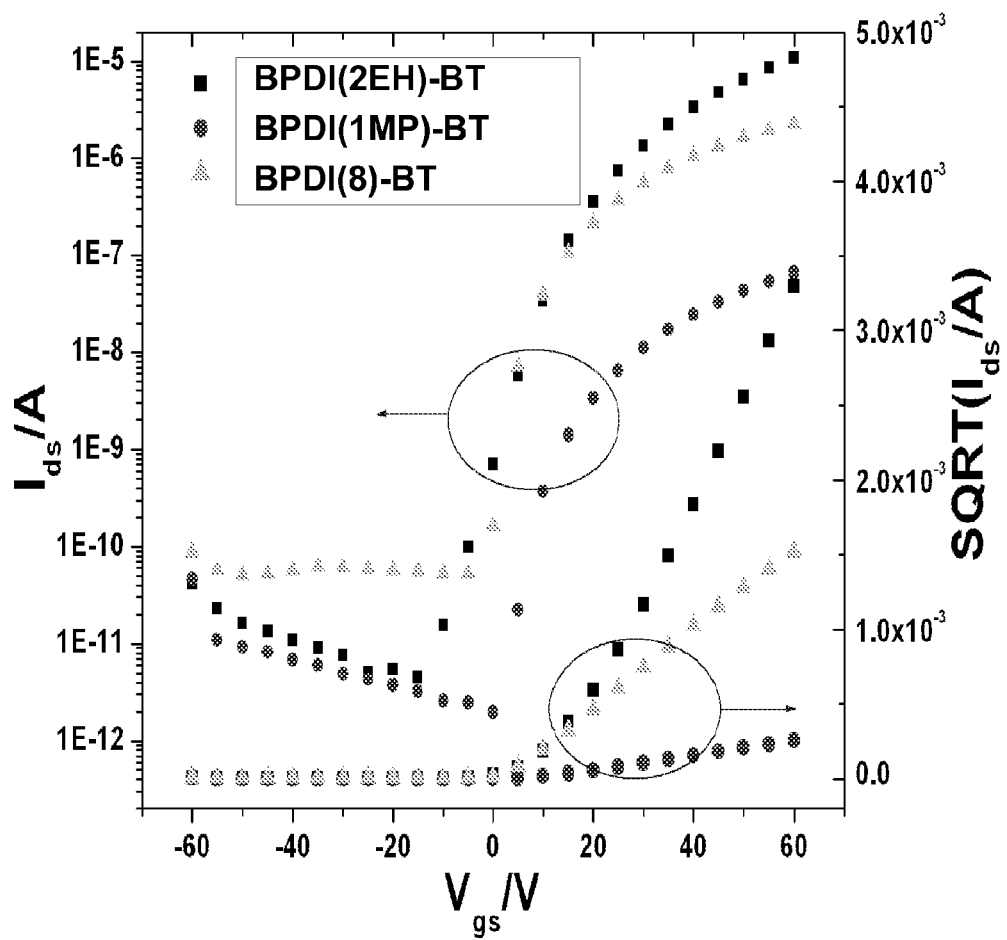
FIG. 6 shows representative output plots obtained with certain bottom-gate top-contact organic field effect transistors according to the present teachings under ambient conditions.

Accordingly, another aspect of the present teachings relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures. FIG. 5 illustrates the four common types of OFET structures: top-contact bottom-gate structure (a), bottom-contact bottom-gate structure (b), bottom-contact top-gate structure (c), and top-contact top-gate structure (d). As shown in FIG. 5, an OFET can include a dielectric layer (e.g., shown as 8, 8', 8", and 8''' in FIGS. 5a, 5b, 5c, and 5d, respectively), a semiconductor layer (e.g., shown as 6, 6', 6", and 6''' in FIGS. 5a, 5b, 5c, and 5d, respectively), a gate contact (e.g., shown as 10, 10', 10", and 10''' in FIGS. 5a, 5b, 5c, and 5d, respectively), a substrate (e.g., shown as 12, 12', 12", and 12''' in FIGS. 5a, 5b, 5c, and 5d, respectively), and source and drain contacts (e.g., shown as 2, 2', 2", 2''', 4, 4', 4", and 4''' in FIGS. 5a, 5b, 5c, and 5d, respectively).

In certain embodiments, OTFT devices can be fabricated with the present compounds on doped silicon substrates, using $SiO_2$ as the dielectric, in top-contact geometries. In particular embodiments, the active semiconductor layer which incorporates at least a compound of the present teachings can be deposited at room temperature or at an elevated temperature. In other embodiments, the active semiconductor layer which incorporates at least a compound of the present teachings can be applied by spin-coating or printing as described herein. For top-contact devices, metallic contacts can be patterned on top of the films using shadow masks.

The following examples are provided to illustrate further and to facilitate the understanding of the present teachings and are not in any way intended to limit the invention.

All reagents were purchased from commercial sources and used without further purification unless otherwise noted. Anhydrous tetrahydrofuran (THF) was distilled from Na/benzophenone. Conventional Schlenk techniques were used and reactions were carried out under $N_2$ unless otherwise noted. Examples 1-4 describe the preparation of certain compounds of the present teachings and related intermediates. Characterization data are provided in some cases by $^1H$ NMR, $^{13}C$ NMR, elemental analysis, and/or electron ionization/electron spray ionization (EI/ESI) mass spectroscopy. NMR spectra were recorded on a Varian Unity Plus 500 spectrometer ($^1H$, 500 MHz; $^{13}C$, 125 MHz). Electrospray mass spectrometry was performed with a Thermo Finnegan model LCQ Advantage mass spectrometer.

EXAMPLE 1

Preparation of 5,5'-bis-[N,N'-bis(1-methylpentyl)-1-cyanoperylene-3,4:9,10-bis(dicarboxiimide)-7-yl]-2,2'-bithiophene (BPDI(1MP)-BT)

Step 1. Preparation of N,N'-bis(1-methylpentyl)-1-bromo-7-cyanoperylene-3,4:9,10-bis(dicarboxiimide) (PDI(1MP)BrCN)

A mixture of N,N'-bis(1-methylpentyl)-1,7-dibromoperylene-3,4:9,10-bis(dicarboxiimide) (PDI1MP-Br$_2$, 1.01 g, 1.41 mmol) and copper(I)cyanide (CuCN) (0.13 g, 1.45 mmol) in dimethylformamide (20 mL) was stirred at 150° C. for 2 hours. After cooling to room temperature, methanol (40 mL) was added to the reaction mixture and the precipitate was collected by filtration and washed with methanol. This crude product (0.88 g) was purified by a column chromatography on silica gel using a mixture of chloroform:hexane (gradient: 2:1 to 4:1 (v/v)) to afford a dark red solid as the product (0.26 g, 0.39 mmol, yield 27.7%).

$^1H$ NMR (CDCl$_3$, 500 MHz): δ 9.69 (d, 1H, J=8.0 Hz), 9.46 (d, 1H, J=8.0 Hz), 8.97 (s, 1H), 8.91(s, 1H), 8.77-8.23 (m, 2H), 5.27-5.30 (m, 2H), 2.23 (s, br, 2H), 1.93 (s, br, 2H), 1.58-1.61 (m, 6H), 1.10-1.20 (m, 8H), 0.88 (s, br, 6H); Elemental Analysis (calc. C, 67.07; H, 4.87; N, 6.34): found C, 67.47; H, 5.09; N, 6.42.

Step 2. Preparation of BPDI(1MP)-BT

Under nitrogen, a mixture of PDI(1MP)BrCN (305 mg, 0 46 mmol), 5,5'-bis(trimethylstannyl)-2,2'-bithiophene (110 mg, 0.22 mmol), and dichlorobis(triphenylphosphine) palladium(II) (Pd(PPh$_3$)$_2$Cl$_2$) (8.1 mg, 0.012 mmol) in anhydrous toluene (20 mL) was stirred at 90° C. for 40 hours. After cooling to room temperature, a solution of potassium fluoride (1.5 g) in water (3 mL) was added, and the resulting mixture was stirred at room temperature for an additional 2 hours. The reaction mixture was extracted with chloroform (100 mL×2) and the organic layers were combined, washed with water, dried over anhydrous sodium sulfate, and concentrated. The residue was purified by a column chromatography on silica gel (dichloromethane:ethyl acetate, gradient 100:1 to 100:3, v/v) to afford a dark solid as the product (221 mg, 0.17 mmol, yield 74.4%).

$^1H$ NMR (CDCl$_3$, 500 MHz): δ 9.44-9.48 (m, 2H), 8.74-8.89 (m, 2H), 8.73-8.80 (m, 4H), 8.45-8.51 (m, 4H), 7.25-7.30 (m, 4H), 5.19-5.40 (m, 4H), 2.05-2.28 (m, 4H), 1.90-1.98 (m, 4H), 1.52-1.64 (m, 12H), 1.20-1.40 (m, 16H), 0.85-0.98 (m, 12H); Elemental Analysis (calc. C, 74.07; 5.15; N, 6.32): found C, 74.12; H, 5.24; N, 6.18.

EXAMPLE 2

Preparation of 5,5'-bis-[N,N'-bisoctyl-1-cyanoperylene-3,4:9,10-bis(dicarboxiimide)-7-yl]-2,2'-bithiophene (BPDI(8)-BT)

Step 1. Preparation of N,N'-bisoctyl-1-bromo-7-cyanoperylene-3,4:9,10-bis(dicarboxiimide) (PDI(8)BrCN)

A mixture of N,N'-bisoctyl-1,7-dibromo-perylene-3,4:9,10-bis(dicarboxiimide) (PDI8-Br$_2$, 2.15 g, 2.78 mmol) and CuCN (0.25 g, 2.79 mmol) in dimethylformamide (50 mL) was stirred at 150° C. for 2 hours. After cooling to room temperature, methanol (50 mL) was added to the reaction mixture and the precipitate was collected by filtration and washed with methanol. This crude product (1.81 g) was purified by a column chromatography on silica gel (chloroform: hexane, 2:1 to 4:1, v/v) to afford a dark red solid as the product (0.44 g, 0.61 mmol, yield 22.0%).

$^1H$ NMR (CDCl$_3$, 500 MHz): δ 9.68 (d, 1H, J=8.0 Hz), 9.45 (d, 1H, J=8.0 Hz), 8.97 (s, 1H), 8.91(s, 1H), 8.82 (d, 1H, J=8.0 Hz), 8.80 (d, 1H, J=8.0 Hz), 4.19-4.23 (m, 4H), 1.74-1.78 (m, 4H), 1.25-1.45 (m, 20H), 0.89 (t, 6H, J=7.0 Hz); Elemental Analysis (calc. C, 68.52; H, 5.61; N, 5.85): found C, 68.72; H, 5.68; N, 5.81.

Step 2. Preparation of BPDI(8)-BT

Under nitrogen, a mixture of PDI(8)BrCN (341 mg, 0 47 mmol), 5,5'-bis(trimethylstannyl)-2,2'-bithiophene (116 mg, 0.24 mmol), and Pd(PPh$_3$)$_2$Cl$_2$ (7.1 mg, 0.010 mmol) in anhydrous toluene (25 mL) was stirred at 90° C. for 44 hours. After cooling to room temperature, a solution of potassium fluoride (1.5 g) in water (3 mL) was added, and the resulting mixture was stirred at room temperature for an additional 2 hours. The reaction mixture was extracted with chloroform (100 mL×2) and the organic layers were combined, washed with water, dried over anhydrous sodium sulfate, and concentrated. The residue was purified by a column chromatography on silica gel (dichloromethane:ethyl acetate, 100:1 to 100:3, v/v) to afford a dark solid as the product (240 mg, 0.17 mmol, yield 70.2%).

$^1H$ NMR (CDCl$_3$, 500 MHz): δ 9.46-9.52 (m, 2H), 8.89-8.90 (m, 2H), 8.75-8.80 (m, 4H), 8.42-8.52 (m, 4H), 7.25-7.30 (m, 4H), 4.13-4.23 (m, 8H), 1.71-1.80 (m, 8H), 1.20-

1.48 (m, 40H), 0.85-0.92 (m, 12H); Elemental Analysis (calc. C, 74.97; H, 5.87; N, 5.83): found C, 74.89; H, 6.01; N, 5.54.

EXAMPLE 3

Preparation of 5,5'-bis-[N,N'-bis(2-ethylhexyl)-1-cyanoperylene-3,4:9,10-bis(dicarboximide)-7-yl]-2,2'-bithiophene (BPDI(2EH)-BT)

Step 1. Preparation of N,N'-bis(2-ethylhexyl)-1-bromo-7-cyanoperylene-3,4:9,10-bis(dicarboximide) (PDI(2EH)BrCN)

A mixture of N,N'-bis(2-ethylhexyl)-1,7-dibromo-perylene-3,4:9,10-bis(dicarboximide) (PDI2EH-Br$_2$, 1.94 g, 2.51 mmol) and CuCN (0.23 g, 2.57 mmol) in dimethylformamide (45 mL) was stirred at 150° C. for 2 hours. After cooling to room temperature, methanol (50 mL) was added to the reaction mixture and the precipitate was then collected by filtration and washed with methanol. This crude product (1.66 g) was purified by a column chromatography on silica gel (chloroform:hexane, 2:1 to 4:1, v/v) to afford a dark red solid as the product (0.38 g, 0.53 mmol, yield 21.1%).

$^1$H NMR (CDCl$_3$, 500 MHz): δ 9.68 (d, 1H, J=8.0 Hz), 9.44 (d, 1H, J=8.0 Hz), 8.97 (s, 1H), 8.90 (s, 1H), 8.81 (d, 1H, J=8.5 Hz), 8.78 (d, 1H, J=8.0 Hz), 4.13-4.18 (m, 4H), 1.96 (s, br, 2H), 1.10-1.50 (m, 16H), 0.90-1.00 (m, 12H); Elemental Analysis (calc. C, 68.52; H, 5.61; N, 5.85): found C, 68.60, H, 5.53; N, 5.84.

Step 2. Preparation of BPDI(2EH)-BT

Under nitrogen, a mixture of PDI(2EH)BrCN (324 mg, 0 45 mmol), 5,5'-bis(trimethylstannyl)-2,2'-bithiophene (110 mg, 0 23 mmol), and Pd(PPh$_3$)$_2$Cl$_2$ (6.4 mg, 0.009 mmol) in anhydrous toluene (20 mL) was stirred at 90° C. for 44 hours. After cooling to room temperature, a solution of potassium fluoride (1.5 g) in water (3 mL) was added, and the resulting mixture was stirred at room temperature for an additional 2 hours. The reaction mixture was extracted with chloroform (100 mL×2) and the organic layers were combined, washed with water, dried over anhydrous sodium sulfate, and concentrated. The residue was purified by a column chromatography on silica gel (dichloromethane:ethyl acetate, 100:1 to 100:3, v/v) to afford a dark solid as the product (272 mg, 0.19 mmol, yield 83.7%).

$^1$H NMR (CDCl$_3$, 500 MHz): δ 9.45-9.48 (m, 2H), 8.90 (s, 2H), 8.74-8.81 (m, 4H), 8.46-8.52 (m, 4H), 7.25-7.30 (m, 4H), 4.05-4.19 (m, 8H), 1.94-2.00 (m, 4H), 1.25-1.41 (m, 32H), 0.85-0.98 (m, 24H); Elemental Analysis (calc. C, 74.97; H, 5.87; N, 5.83): found C, 75.34; H, 6.04; N, 5.60.

EXAMPLE 4

Preparation of 5,5'-bis-[N,N'-bis(1-methylpentyl)-1-cyanoperylene-3,4:9,10-bis(dicarboximide)-7-yl]-4,7-benzothiadiazole (BPDI(1MP)-BTZ)

A mixture of benzothiadiazole dibronic ester (38 mg, 0.098 mmol), PDI1MPBrCN (0.13 g, 0.19 mmol), Pd(PPh$_3$)$_4$ (13 mg, 0.011 mmol), potassium carbonate aqueous solution (2 M, 4.5 mL), aliquat 336 (20 mg), and anhydrous toluene (6 mL) was stirred at 105 ° C. under Ar for 44 h. After cooling to room temperature, the reaction mixture was extracted with CHCl$_3$ (50 mL×2). The combined organic layers were washed with water, dried over anhydrous Na$_2$SO$_4$, and concentrated on a rotary evaporator. The resulting residue was purified by column chromatography on silica gel with CH$_2$Cl$_2$ (slowly up to CH$_2$Cl$_2$:ethyl acetate=100:5, v/v) as the eluent to afford an orange/red solid as the product (4.0 mg, 0.0031 mmol, yield 3.2%).

$^1$H NMR (CDCl$_3$, 500 MHz): δ 9.78 (d, 2H, J=8 Hz), 8.89 (s, 2H), 8.71-8.82 (m, 10H), 5.25-5.34 (m, 4H), 2.18-2.28 (m, 4H), 1.90-2.00 (m, 4H), 1.58-1.68 (m, 12H), 1.20-1.40 (m, 16H), 0.86-0.92 (m, 12H).

EXAMPLE 5

Thermal Properties

The thermal properties of certain bispolycyclic compounds (e.g., dimeric perylene) were examined by differential scanning calorimetry. The endotherm and the exotherm are reversible and readily reproducible for the BPDI(1MP)-BT, indicating a melting and re-crystallization process. For the other compounds, irreversible thermal processes were observed.

EXAMPLE 6

Solubility

All of the mono-bromo mono-cyano perylenes and dimeric perylenes are sufficiently soluble for processing in conventional organic solvents such as chloroform, xylene, dichlorobenzene, and anisole. Table 1 shows the solubility data in dichlorobenzene at 60° C. for certain compounds of the present teachings.

TABLE 1

| Compound | Solubility (mg/mL) |
|---|---|
| BPDI(2EH)-BT | 5.5 |
| BPDI(1MP)-BT | 33.9 |
| BPDI(8)-BT | 7.8 |

EXAMPLE 7

Transistor Device Fabrication and Characterization

Bottom-gate top contact OFETs were fabricated using compounds of the present teachings as the semiconductor layer. Prime grade n-doped silicon wafers (100) having 300 nm of thermally grown oxide (Process Specialties Inc.) were used as device substrates. These were rinsed with water, methanol, and acetone before film deposition. Trimethylsilyl functionalization of the Si/SiO$_2$ surface was carried out by exposing the silicon wafers to hexamethyldisilazane (HMDS) vapor at room temperature in a closed container under nitrogen overnight. Thin films of mono-bromo mono-cyano perylenes were prepared by vapor deposition and spin-coating, and thin films of the dimeric perylenes were prepared by spin coating only. Different solvents and solvent mixtures can be used for semiconductor film deposition. The gate region was accessed by an ohmic contact to the Si substrate, and the gold source and drain contacts were prepared by vapor deposition through a shadow mask onto the semiconductor layer.

All electrical measurements were performed in ambient atmosphere. To allow comparison with other organic FETs, mobilities (μ) were calculated by standard field effect transistor equations. In traditional metal-insulator-semiconductor FETs (MISFETs), there is typically a linear and saturated regime in the I$_{DS}$ vs V$_{DS}$ curves at different V$_G$ (where I$_{DS}$ is the source-drain saturation current, $V_{DS}$ is the potential between the source and drain, and $V_G$ is the gate voltage). At large $V_{DS}$, the current saturates and is given by:

$$(I_{DS})_{sat} = (WC_i/2L)\mu(V_G - V_t)^2 \qquad (1)$$

where L and W are the device channel length and width, respectively, $C_i$ is the capacitance of the oxide insulator (~10 nF/cm² for ~300 nm $SiO_2$), and $V_t$ is the threshold voltage. Mobilities (μ) were calculated in the saturation regime by rearranging equation (1):

$$\mu_{sat} = (2I_{DS}L)/[WC_i(V_G - V_t)^2] \qquad (2)$$

The threshold voltage ($V_t$) can be estimated as the X-axis intercept of the linear section of the plot of $V_G$ versus $(I_{DS})^{1/2}$ (at $V_{SD} = -100$ V).

Tables 2a and 2b shows device characteristics (including field effect mobility and current on/off ratio) of certain OFETs fabricated with mono-bromo mono-cyano perylenes via vacuum deposition (Table 2a) and spin-coating from chloroform solution at a concentration of about 8 mg/mL (Table 2b). All semiconductors exhibit n-channel (electron) transport when the devices were tested in ambient conditions.

TABLE 2a

| Compound | Mobility (cm²/Vs) | Current On/Off Ratio | Current On/Off Ratio (0 V) |
|---|---|---|---|
| PDI(8)BrCN | 1.78E−02 | 1.8E+05 | 1.6E+05 |
| PDI(2EH)BrCN | 3.03E−03 | 7.6E+03 | 6.7E+03 |
| PDI(1MP)BrCN | 8.78E−04 | 1.7E+04 | 1.7E+04 |

TABLE 2b

| Compound | Mobility (cm²/Vs) | Current On/Off Ratio | Current On/Off Ratio (0 V) |
|---|---|---|---|
| PDI(8)BrCN | 1.10E−04 | 2.8E+03 | 2.8E+03 |
| PDI(2EH)BrCN | 3.90E−04 | 1.3E+04 | 1.3E+04 |
| PDI(1MP)BrCN | 5.13E−03 | 1.1E+04 | 1.1E+04 |

Table 3 shows device characteristics (including field effect mobility and current on/off ratio) of certain OFETs fabricated with dimeric perylenes via spin-coating from a chloroform/dichlorobenzene (98:2, w/w) solution at a concentration of about 8 mg/mL. All semiconductors exhibit n-channel (electron) transport when the devices were tested in ambient conditions. It was observed that the dimeric perylenes tested provided solutions with an unexpectedly wide range of viscosity, which facilitated the device fabrication process.

TABLE 3

| Compound | Mobility (cm²/Vs) | Current On/Off Ratio | $V_{TH}$ (V) |
|---|---|---|---|
| BPDI(8)-BT | 8.7E−03 | 2.4E+04 | −5 |
| BPDI(2EH)-BT | 0.05 | 2.4E+06 | −15 |
| BPDI(1MP)-BT | 2.6E−04 | 3.3E+04 | 0 |

The present teachings encompass embodiments in other specific forms without departing from the spirit or essential characteristics thereof The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

The invention claimed is:
1. A compound having Formula I:

wherein:
Q and Q' independently are:

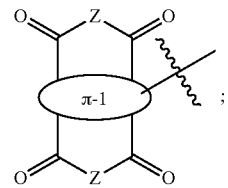

and
wherein:
π-1 is a perylene moiety optionally substituted with 1-8 $R^a$ groups;
Z, at each occurrence, is selected from the group consisting of a) O, b) S, c) $NR^b$, d) C(O), and e) $CR^cR^d$;
$R^a$, at each occurrence, is a) halogen, b) —CN, c) —$NO_2$, d) —$OR^f$, e) —$SR^f$, f) —$NR^gR^h$, g) —N(O)$R^gR^h$, h) —S(O)$_mR^g$, i) —S(O)$_mOR^g$, j) —S(O)$_mN$R$^gR^h$, k) —C(O)$R^g$, l) —C(O)$OR^f$, m) —C(O)NR$^g$R$^h$, n) —C(S)NR$^gR^h$, o) —$SiH_3$, p) —SiH($C_{1-20}$alkyl)$_2$, q) —$SiH_2$($C_{1-20}$alkyl), r) —Si($C_{1-20}$alkyl)$_3$, s) a $C_{1-20}$alkyl group, t) a $C_{2-20}$alkenyl group, u) a $C_{2-20}$alkynyl group, v) a $C_{1-20}$haloalkyl group, w) a —Y—$C_{3-14}$cycloalkyl group, x) a —Y—$C_{6-14}$aryl group, y) a —Y-3-14 membered cycloheteroalkyl group, or z) a —Y-5-14 membered heteroaryl group, wherein each of the $C_{1-20}$alkyl group, the $C_{2-20}$alkenyl group, the $C_{2-20}$alkynyl group, the $C_{3-14}$cycloalkyl group, the $C_{6-14}$aryl group, the 3-14 membered cycloheteroalkyl group, and the 5-14 membered heteroaryl group optionally is substituted with 1-4 $R^i$ groups;
$R^b$, at each occurrence, is a) H, b) —($CH_2CH_2O$)$_q$H, c) —($CH_2CH_2O$)$_q$—$CH_3$, d) —C(O)$OR^f$, e) —C(O)$R^g$, f) —C(O)NR$^gR^h$, g) —C(S)$OR^f$, h) —C(S)$R^g$, i) —C(S)NR$^gR^h$, j) —S(O)$_mR^g$, k) —S(O)$_mOR^g$, l) a $C_{1-20}$alkyl group, m) a $C_{2-20}$alkenyl group, n) a $C_{2-20}$alkynyl group, o) a $C_{1-20}$alkoxy group, p) a —Y—$C_{3-14}$cycloalkyl group, q) a —Y—$C_{6-14}$aryl group, r) a —Y-3-14 membered cycloheteroalkyl group, or s) a —Y-5-14 membered heteroaryl group, wherein each of the $C_{1-20}$alkyl group, the $C_{2-20}$alkenyl group, the $C_{2-20}$alkynyl group, the $C_{1-20}$alkoxy group, the $C_{3-14}$cycloalkyl group, the $C_{6-14}$aryl group, the 3-14 membered cycloheteroalkyl group, and the 5-14 membered heteroaryl group optionally is substituted with 1-4 $R^i$ groups;
$R^c$ and $R^d$, at each occurrence, independently are a) H, b) halogen, c) —($CH_2CH_2O$)$_q$H, d —($CH_2CH_2O$)$_q$—$CH_3$, e) a $C_{1-20}$alkoxy group, f) a $C_{1-20}$alkyl group, g) a $C_{2-20}$alkenyl group, h) a $C_{2-20}$alkynyl group, i) a —Y—$C_{3-14}$cycloalkyl group, j) a —Y—$C_{6-14}$aryl group, k) a —Y-3-14 membered cycloheteroalkyl group, or l) a —Y-5-14 membered heteroaryl group, wherein each of the $C_{1-20}$alkyl group, the $C_{2-20}$alkenyl group, the $C_{2-20}$alkynyl group, the $C_{3-14}$cycloalkyl group, the $C_{6-14}$aryl group, the 3-14 membered cycloheteroalkyl group, and the 5-14 membered heteroaryl group optionally is substituted with 1-4 $R^i$ groups;

R$^f$, at each occurrence, is a) H, b) —C(O)R$^g$, c) —C(O)NR$^g$R$^h$, d) —C(S)R$^g$, e) —C(S)NR$^g$R$^h$, f) a C$_{1-20}$alkyl group, g) a C$_{2-20}$alkenyl group, h) a C$_{2-20}$alkynyl group, i) a C$_{3-14}$cycloalkyl group, j) a C$_{6-14}$aryl group, k) a 3-14 membered cycloheteroalkyl group, or l) a 5-14 membered heteroaryl group, wherein each of the C$_{1-20}$alkyl group, the C$_{2-20}$alkenyl group, the C$_{2-20}$alkynyl group, the C$_{3-14}$cycloalkyl group, the C$_{6-14}$ aryl group, the 3-14 membered cycloheteroalkyl group, and the 5-14 membered heteroaryl group optionally is substituted with 1-4 R$^i$ groups;

R$^g$ and R$^h$, at each occurrence, independently are a) H, b) —OH, c) —SH, d) —S(O)$_2$OH, e) —C(O)OH, f) —C(O)NH$_2$, g) —C(S)NH$_2$, h) —OC$_{1-10}$alkyl, i) —C(O)—C$_{1-20}$ alkyl, j) —C(O)—OC$_{1-20}$alkyl, k) —C(S)N(C$_{1-20}$alkyl)$_2$, l) —C(S)NH—C$_{1-20}$alkyl, m) —C(O)NH—C$_{1-20}$alkyl, n) —C(O)N(C$_{1-20}$alkyl)$_2$, o) —S(O)$_m$—C$_{1-20}$alkyl, p) —S(O)$_m$—OC$_{1-20}$ alkyl, q) a C$_{1-20}$alkyl group, r) a C$_{2-20}$alkenyl group, s) a C$_{2-20}$alkynyl group, t) a C$_{1-20}$ alkoxy group, u) a C$_{3-14}$cycloalkyl group, v) a C$_{6-14}$aryl group, w) a 3-14 membered cycloheteroalkyl group, or x) a 5-14 membered heteroaryl group, wherein each of the C$_{1-20}$alkyl groups, the C$_{2-20}$alkenyl group, the C$_{2-20}$alkynyl group, the C$_{3-14}$ cycloalkyl group, the C$_{6-14}$aryl group, the 3-14 membered cycloheteroalkyl group, and the 5-14 membered heteroaryl group optionally is substituted with 1-4 R$^i$ groups;

R$^i$, at each occurrence, is a) halogen, b) —CN, c) —NO$_2$, d) oxo, e) —OH, f) —NH$_2$, g) —NH(C$_{1-20}$ alkyl), h) —N(C$_{1-20}$alkyl)$_2$, i) —N(C$_{1-20}$alkyl)-C$_{6-14}$ aryl, j) —N(C$_{6-14}$aryl)$_2$, k) —S(O)$_m$H, l) —S(O)$_m$—C$_{1-20}$alkyl, m) —S(O)$_2$OH, n) —S(O)$_m$—OC$_{1-20}$ alkyl, o) —S(O)$_m$—OC$_{6-14}$aryl, p) —CHO, q) —C(O)—C$_{1-20}$alkyl, r) —C(O)-C$_{6-14}$aryl, s) —C(O)OH, t) —C(O)—OC$_{1-20}$alkyl, u) —C(O)—CO$_{6-14}$ aryl, v) —C(O)NH$_2$, w) —C(O)NH—C$_{1-20}$alkyl, x) —C(O)N(C$_{1-20}$alkyl)$_2$, y) —C(O)NH—C$_{6-14}$aryl, z) —C(O)N(C$_{1-20}$alkyl)-C$_{6-14}$aryl, aa) —C(O)N(C$_{6-14}$ aryl)$_2$, ab) —C(S)NH$_2$, ac) —(C(S)NH—C$_{1-20}$alkyl, ad) —C(S)N(C$_{1-20}$alkyl)$_2$, ae) —C(S)N(C$_{6-14}$aryl)$_2$, af) —C(S)N(C$_{1-20}$alkyl)-C$_{6-14}$aryl, ag) —C(S)NH—C$_{6-14}$ aryl, ah) —S(O)$_m$NH$_2$, ai) —S(O)$_m$NH(C$_{1-20}$ alkyl), aj) —S(O$_m$N(C$_{1-20}$alkyl)$_2$, ak) —S(O)$_m$NH (C$_{6-14}$aryl), al) —S(O)$_m$N(C$_{1-20}$alkyl)-C$_{6-14}$aryl, am) —S(O)$_m$N(C$_{6-14}$aryl)$_2$, an) —SiH$_3$, ao) —SiH(C$_{1-20}$ alkyl)$_2$, ap) —SiH$_2$(C$_{1-20}$alkyl), ar) —Si(C$_{1-20}$ alkyl)$_3$, as) a C$_{1-20}$alkoxy group, at) a C$_{2-20}$alkenyl group, au) a C$_{2-20}$alkynyl group, av) a C$_{1-20}$alkoxy group, aw) a C$_{1-20}$alkylthio group, ax) a C$_{1-20}$haloalkyl group, ay) a C$_{3-14}$cycloalkyl group, az) a C$_{6-14}$aryl group, ba) a 3-14 membered cycloheteroalkyl group, or bb) a 5-14 membered heteroaryl group;

Y, at each occurrence, is a) a divalent C$_{1-20}$alkyl group, b) a divalent C$_{1-20}$ haloalkyl group, or c) a covalent bond;

m, at each occurrence, is 0, 1, or 2 and q, at each occurrence, is an integer in the range of 1 to 20, L is selected from the group consisting of b) —(Ar$^2$)$_{n'}$—, c) —(Ar$^1$)$_n$—(Ar$^2$)$_{n'}$—(Ar$^1$)$_{n''}$—, and d) —(Ar$^2$)$_{n'}$—(Ar$^1$)$_n$—(Ar$^2$)$_{n''}$—, wherein:

Ar$^1$, at each occurrence, independently is a 5- or 6-membered aryl or heteroaryl group, each optionally substituted with 1-4 R$^i$ groups;

Ar$^2$, at each occurrence, independently is selected from an optionally substituted polycyclic 8-22 membered aryl or heteroaryl group comprising at least one phenyl, thienyl, or thiazolyl group fused to a moiety selected from the group consisting of:

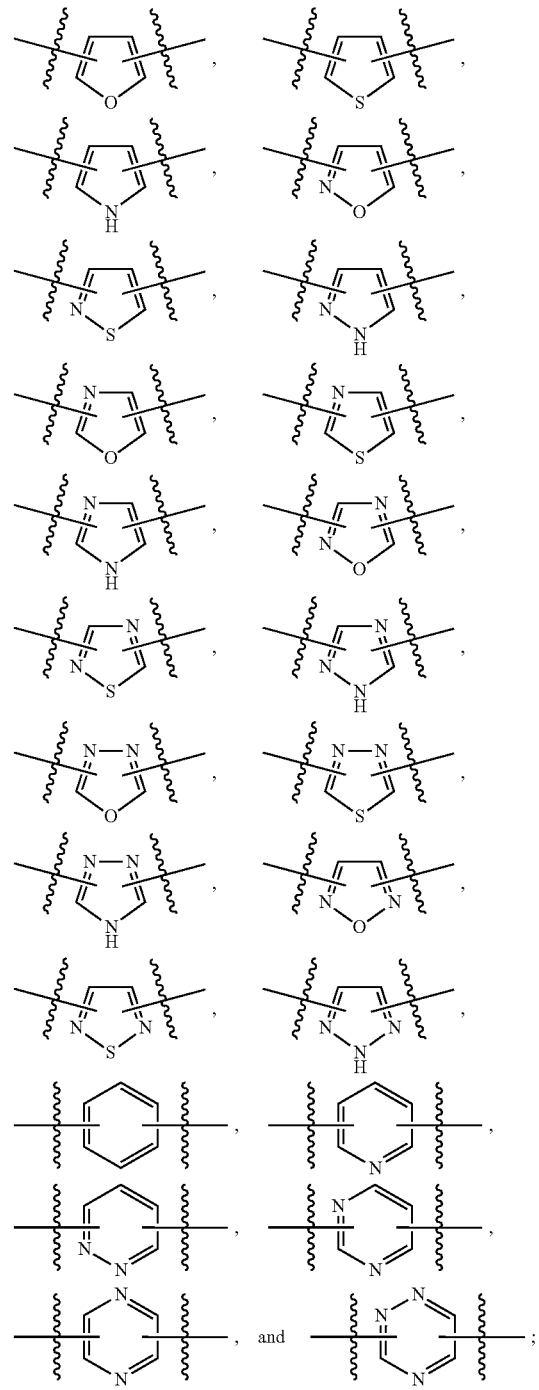

and n, n', and n'' independently are 1, 2, 3, 4, 5, or 6.

2. A compound having Formula I:

Q-L-Q'  I, wherein:

Q and Q' independently are:

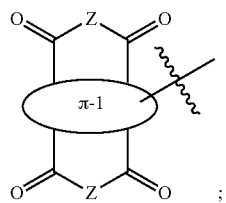

and wherein:

π-1 is a perylene moiety optionally substituted with 1-8 $R^a$ groups;

Z, at each occurrence, is selected from the group consisting of a) O, b) S, c) $NR^b$, d) C(O), and e) $CR^cR^d$;

$R^a$, at each occurrence, is a) halogen, b) —CN, c) —NO$_2$, d) —OR$^f$, e) —SR$^f$, f) —NR$^g$R$^h$, g) —N(O)R$^g$R$^h$, h) —S(O)$_m$R$^g$, i) —S(O)$_m$OR$^g$, j) —S(O)$_m$NR$^g$R$^h$, k) —C(O)R$^g$, l) —C(O)OR$^f$, m) —C(O)NR$^g$R$^h$, n) —C(S)NR$^g$R$^h$, o) —SiH$_3$, p) —SiH(C$_{1-20}$alkyl)$_2$, q) —SiH$_2$(C$_{1-20}$alkyl), r) —Si(C$_{1-20}$alkyl)$_3$, s) a C$_{1-20}$alkyl group, t) a C$_{2-20}$alkenyl group, u) a C$_{2-20}$alkynyl group, v) a C$_{1-20}$haloalkyl group, w) a —Y—C$_{3-14}$cycloalkyl group, x) a —Y—C$_{6-14}$aryl group, y) a —Y-3-14 membered cycloheteroalkyl group, or z) a —Y-5-14 membered heteroaryl group, wherein each of the C$_{1-20}$alkyl group, the C$_{2-20}$alkenyl group, the C$_{2-20}$alkynyl group, the C$_{3-14}$cycloalkyl group, the C$_{6-14}$aryl group, the 3-14 membered cycloheteroalkyl group, and the 5-14 membered heteroaryl group optionally is substituted with 1-4 $R^i$ groups;

$R^b$, at each occurrence, is a) H, b) —(CH$_2$CH$_2$O)$_q$H, c) —(CH$_2$CH$_2$O)$_q$—CH$_3$, d) —C(O)OR$^f$, e) —C(O)R$^g$, f) —C(O)NR$^g$R$^h$, g) —C(S)OR$^f$, h) —C(S)R$^g$, i) —C(S)NR$^g$R$^h$, j) —S(O)$_m$R$^g$, k) —S(O)$_m$OR$^g$, l) a C$_{1-20}$alkyl group, m) a C$_{2-20}$alkenyl group, n) a C$_{2-20}$ alkynyl group, o) a C$_{1-20}$alkoxy group, p) a —Y—C$_{3-14}$cycloalkyl group, q) a —Y—C$_{6-14}$aryl group, r) a —Y-3-14 membered cycloheteroalkyl group, or s) a —Y-5-14 membered heteroaryl group, wherein each of the C$_{1-20}$alkyl group, the C$_{2-20}$alkenyl group, the C$_{2-20}$alkynyl group, the C$_{1-20}$alkoxy group, the C$_{3-14}$cycloalkyl group, the C$_{6-14}$aryl group, the 3-14 membered cycloheteroalkyl group, and the 5-14 membered heteroaryl group optionally is substituted with 1-4 $R^i$ groups;

$R^c$ and $R^d$, at each occurrence, independently are a) H, b) halogen, c) —(CH$_2$CH$_2$O)$_q$H, d —(CH$_2$CH$_2$O)$_q$—CH$_3$, e) a C$_{1-20}$alkoxy group, f) a C$_{1-20}$alkyl group, g) a C$_{2-20}$alkenyl group, h) a C$_{2-20}$alkynyl group, i) a —Y—C$_{3-14}$cycloalkyl group, j) a —Y—C$_{6-14}$aryl group, k) a —Y-3-14 membered cycloheteroalkyl group, or l) a —Y-5-14 membered heteroaryl group, wherein each of the C$_{1-20}$alkyl group, the C$_{2-20}$alkenyl group, the C$_{2-20}$alkynyl group, the C$_{3-14}$cycloalkyl group, the C$_{6-14}$aryl group, the 3-14 membered cycloheteroalkyl group, and the 5-14 membered heteroaryl group optionally is substituted with 1-4 $R^i$ groups;

$R^f$, at each occurrence, is a) H, b) —C(O)R$^g$, c) —C(O)NR$^g$R$^h$, d) —C(S)R$^g$, e) —C(S)NR$^g$R$^h$, f) a C$_{1-20}$alkyl group, g) a C$_{2-20}$alkenyl group, h) a C$_{2-20}$alkynyl group, i) a C$_{3-14}$cycloalkyl group, j) a C$_{6-14}$aryl group, k) a 3-14 membered cycloheteroalkyl group, or l) a 5-14 membered heteroaryl group, wherein each of the C$_{1-20}$alkyl group, the C$_{2-20}$alkenyl group, the C$_{2-20}$alkynyl group, the C$_{3-14}$cycloalkyl group, the C$_{6-14}$ aryl group, the 3-14 membered cycloheteroalkyl group, and the 5-14 membered heteroaryl group optionally is substituted with 1-4 $R^i$ groups;

$R^g$ and $R^h$, at each occurrence, independently are a) H, b) —OH, c) —SH, d) —S(O)$_2$OH, e) —C(O)OH, f) —C(O)NH$_2$, g) —C(S)NH$_2$, h) —OC$_{1-10}$alkyl, i) —C(O)—C$_{1-20}$ alkyl, j) —C(O)—OC$_{1-20}$alkyl, k) —C(S)N(C$_{1-20}$alkyl)$_2$, l) —C(S)NH—C$_{1-20}$alkyl, m) —C(O)NH—C$_{1-20}$alkyl, n) —C(O)N(C$_{1-20}$alkyl)$_2$, o) —S(O)$_m$—C$_{1-20}$alkyl, p) —S(O)$_m$—OC$_{1-20}$ alkyl, q) a C$_{1-20}$alkyl group, r) a C$_{2-20}$alkenyl group, s) a C$_{2-20}$alkynyl group, t) a C$_{1-20}$ alkoxy group, u) a C$_{3-14}$cycloalkyl group, v) a C$_{6-14}$aryl group, w) a 3-14 membered cycloheteroalkyl group, or x) a 5-14 membered heteroaryl group, wherein each of the C$_{1-20}$alkyl groups, the C$_{2-20}$alkenyl group, C$_{2-20}$alkynyl group, the C$_{3-14}$ cycloalkyl group, the C$_{6-14}$aryl group, the 3-14 membered cycloheteroalkyl group, and the 5-14 membered heteroaryl group optionally is substituted with 1-4 $R^i$ groups;

$R^i$, at each occurrence, is a) halogen, b) —CN, c) —NO$_2$, d) oxo, e) —OH, f) —NH$_2$, g) —NH(C$_{1-20}$alkyl), h) —N(C$_{1-20}$alkyl)$_2$, i) —N(C$_{1-20}$alkyl)-C$_{6-14}$aryl, j) —N(C$_{6-14}$aryl)$_2$, k) —S(O)$_m$H, l) —S(O)$_m$—C$_{1-20}$alkyl, m) —S(O)$_2$OH, n) —S(O)$_m$—OC$_{1-20}$alkyl, o) —S(O)$_m$—OC$_{6-14}$aryl, p) —CHO, q) —C(O)—C$_{1-20}$alkyl, r) —C(O)-C$_{6-14}$aryl, s) —C(O)OH, t) —C(O)—OC$_{1-20}$alkyl, u) —C(O)—CO$_{6-14}$aryl, v) —C(O)NH$_2$, w) —C(O)NH—C$_{1-20}$alkyl, x) —C(O)N(C$_{1-20}$alkyl)$_2$, y) —C(O)NH—C$_{6-14}$aryl, z) —C(O)N(C$_{1-20}$alkyl)-C$_{6-14}$aryl, aa) —C(O)N(C$_{6-14}$aryl)$_2$, ab) —C(S)NH$_2$, ac) —C(S)NH—C$_{1-20}$alkyl, ad) —C(S)N(C$_{1-20}$alkyl)$_2$, ae) —C(S)N(C$_{6-14}$aryl)$_2$, af) —C(S)N(C$_{1-20}$alkyl)-C$_{6-14}$aryl, ag) —C(S)NH—C$_{6-14}$ aryl, ah) —S(O)$_m$NH$_2$, ai) —S(O)$_m$NH(C$_{1-20}$alkyl), aj) —S(O$_m$N(C$_{1-20}$alkyl)$_2$, ak) —S(O)$_m$NH(C$_{6-14}$aryl), al) —S(O)$_m$N(C$_{1-20}$alkyl)-C$_{6-14}$aryl, am) —S(O)$_m$N(C$_{6-14}$aryl)$_2$, an) —SiH$_3$, ao) —SiH(C$_{1-20}$alkyl)$_2$, ap) —SiH$_2$(C$_{1-20}$alkyl), ar) —Si(C$_{1-20}$alkyl)$_3$, as) a C$_{1-20}$alkoxy group, at) a C$_{2-20}$alkenyl group, au) a C$_{2-20}$alkynyl group, av) a C$_{1-20}$alkoxy group, aw) a C$_{1-20}$alkylthio group, ax) a C$_{1-20}$haloalkyl group, ay) a C$_{3-14}$cycloalkyl group, az) a C$_{6-14}$aryl group, ba) a 3-14 membered cycloheteroalkyl group, or bb) a 5-14 membered heteroaryl group;

Y, at each occurrence, is a) a divalent C$_{1-20}$alkyl group, b) a divalent C$_{1-20}$ haloalkyl group, or c) a covalent bond;

m, at each occurrence, is 0, 1, or 2 and q, at each occurrence, is an integer in the range of 1 to 20, L is —(Ar$^1$)$_n$— and is selected from the group consisting of:

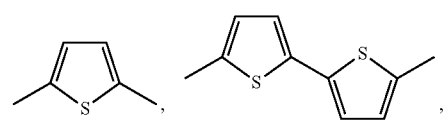

-continued
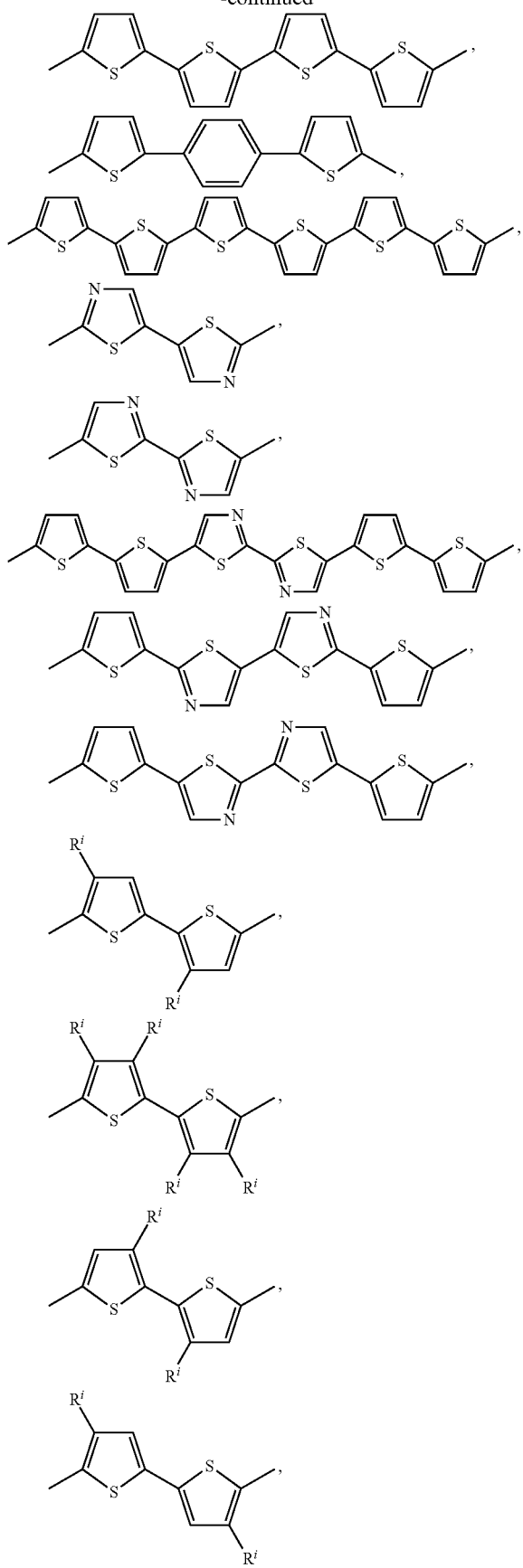
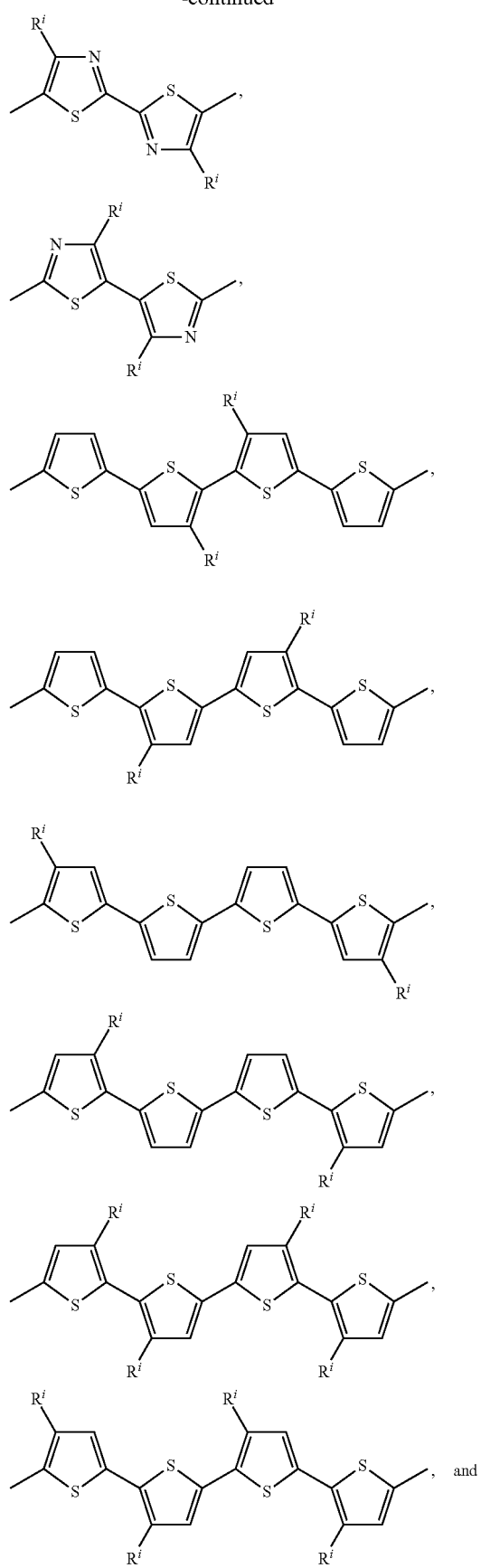

-continued

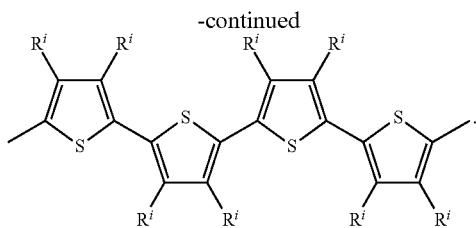

3. A compound having Formula I:

Q-L-Q'  I, wherein:
Q and Q' independently are:

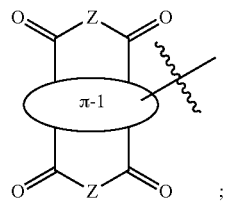

and
wherein:
π-1 is a perylene moiety optionally substituted with 1-8 $R^a$ groups;
Z, at each occurrence, is selected from the group consisting of a) O, b) S, c) $NR^b$, d) C(O), and e) $CR^cR^d$;
$R^a$, at each occurrence, is a) halogen, b) —CN, c) —$NO_2$, d) —$OR^f$, e) —$SR^f$, f) —$NR^gR^h$, g) —N(O)$R^gR^h$, h) —S(O)$_m R^g$, i) —S(O)$_m OR^g$, j) —S(O)$_m N$-$R^gR^h$, k) —C(O)$R^g$, l) —C(O)$OR^f$, m) —C(O)$NR^g$$R^h$, n) —C(S)$NR^gR^h$, o) —$SiH_3$, p) —SiH($C_{1-20}$alkyl)$_2$, q) —SiH$_2$($C_{1-20}$alkyl), r) —Si($C_{1-20}$alkyl)$_3$, s) a $C_{1-20}$alkyl group, t) a $C_{2-20}$alkenyl group, u) a $C_{2-20}$alkynyl group, v) a $C_{1-20}$haloalkyl group, w) a —Y—$C_{3-14}$cycloalkyl group, x) a —Y—$C_{6-14}$aryl group, y) a —Y-3-14 membered cycloheteroalkyl group, or z) a —Y-5-14 membered heteroaryl group, wherein each of the $C_{1-20}$alkyl group, the $C_{2-20}$alkenyl group, the $C_{2-20}$alkynyl group, the $C_{3-14}$cycloalkyl group, the $C_{6-14}$aryl group, the 3-14 membered cycloheteroalkyl group, and the 5-14 membered heteroaryl group optionally is substituted with 1-4 $R^i$ groups;
$R^b$, at each occurrence, is a) H, b) —($CH_2CH_2O)_q$H, c) —($CH_2CH_2O)_q$—$CH_3$, d) —C(O)$OR^f$, e) —C(O)$R^g$, f) —C(O)$NR^gR^h$, g) —C(S)$OR^f$, h) —C(S)$R^g$, i) —C(S)$NR^gR^h$, j) —S(O)$_m R^g$, k) —S(O)$_m OR^g$, l) a $C_{1-20}$alkyl group, m) a $C_{2-20}$alkenyl group, n) a $C_{2-20}$alkynyl group, o) a $C_{1-20}$alkoxy group, p) a —Y—$C_{3-14}$cycloalkyl group, q) a —Y—$C_{6-14}$aryl group, r) a —Y-3-14 membered cycloheteroalkyl group, or s) a —Y-5-14 membered heteroaryl group, wherein each of the $C_{1-20}$alkyl group, the $C_{2-20}$alkenyl group, the $C_{2-20}$alkynyl group, the $C_{1-20}$alkoxy group, the $C_{3-14}$cycloalkyl group, the $C_{6-14}$aryl group, the 3-14 membered cycloheteroalkyl group, and the 5-14 membered heteroaryl group optionally is substituted with 1-4 $R^i$ groups;
$R^c$ and $R^d$, at each occurrence, independently are a) H, b) halogen, c) —($CH_2CH_2O)_q$H, d —($CH_2CH_2O)_q$—$CH_3$, e) a $C_{1-20}$alkoxy group, f) a $C_{1-20}$alkyl group, g) a $C_{2-20}$alkenyl group, h) a $C_{2-20}$alkynyl group, i) a —Y—$C_{3-14}$cycloalkyl group, j) a —Y—$C_{6-14}$aryl group, k) a —Y-3-14 membered cycloheteroalkyl group, or l) a —Y-5-14 membered heteroaryl group, wherein each of the $C_{1-20}$alkyl group, the $C_{2-20}$alkenyl group, the $C_{2-20}$alkynyl group, the $C_{3-14}$cycloalkyl group, the $C_{6-14}$aryl group, the 3-14 membered cycloheteroalkyl group, and the 5-14 membered heteroaryl group optionally is substituted with 1-4 $R^i$ groups;
$R^f$, at each occurrence, is a) H, b) —C(O)$R^g$, c) —C(O)$NR^gR^h$, d) —C(S)$R^g$, e) —C(S)$NR^gR^h$, f) a $C_{1-20}$alkyl group, g) a $C_{2-20}$alkenyl group, h) a $C_{2-20}$alkynyl group, i) a $C_{3-14}$cycloalkyl group, j) a $C_{6-14}$aryl group, k) a 3-14 membered cycloheteroalkyl group, or l) a 5-14 membered heteroaryl group, wherein each of the $C_{1-20}$alkyl group, the $C_{2-20}$alkenyl group, the $C_{2-20}$alkynyl group, the $C_{3-14}$cycloalkyl group, the $C_{6-14}$ aryl group, the 3-14 membered cycloheteroalkyl group, and the 5-14 membered heteroaryl group optionally is substituted with 1-4 $R^i$ groups;
$R^g$ and $R^h$, at each occurrence, independently are a) H, b) —OH, c) —SH, d) —S(O)$_2$OH, e) —C(O)OH, f) —C(O)$NH_2$, g) —C(S)$NH_2$, h) —$OC_{1-10}$alkyl, i) —C(O)—$C_{1-20}$ alkyl, j) —C(O)—$OC_{1-20}$alkyl, k) —C(S)N($C_{1-20}$alkyl)$_2$, l) —C(S)NH—$C_{1-20}$alkyl, m) —C(O)NH—$C_{1-20}$alkyl, n) —C(O)N($C_{1-20}$alkyl)$_2$, o) —S(O)$_m$—$C_{1-20}$alkyl, p) —S(O)$_m$—$OC_{1-20}$ alkyl, q) a $C_{1-20}$alkyl group, r) a $C_{2-20}$alkenyl group, s) a $C_{2-20}$alkynyl group, t) a $C_{1-20}$ alkoxy group, u) a $C_{3-14}$cycloalkyl group, v) a $C_{6-14}$aryl group, w) a 3-14 membered cycloheteroalkyl group, or x) a 5-14 membered heteroaryl group, wherein each of the $C_{1-20}$alkyl groups, the $C_{2-20}$alkenyl group, the $C_{2-20}$alkynyl group, the $C_{3-14}$ cycloalkyl group, the $C_{6-14}$aryl group, the 3-14 membered cycloheteroalkyl group, and the 5-14 membered heteroaryl group optionally is substituted with 1-4 $R^i$ groups;
$R^i$, at each occurrence, is a) halogen, b) —CN, c) —$NO_2$, d) oxo, e) —OH, f) —$NH_2$, g) —NH($C_{1-20}$alkyl), h) —N($C_{1-20}$alkyl)$_2$, i) —N($C_{1-20}$alkyl)-$C_{6-14}$aryl, j) —N($C_{6-14}$aryl)$_2$, k) —S(O)$_m$H, l) —S(O)$_m$—$C_{1-20}$alkyl, m) —S(O)$_2$OH, n) —S(O)$_m$—$OC_{1-20}$alkyl, o) —S(O)$_m$—$OC_{6-14}$aryl, p) —CHO, q) —C(O)—$C_{1-20}$alkyl, r) —C(O)-$C_{6-14}$aryl, s) —C(O)OH, t) —C(O)—$OC_{1-20}$alkyl, u) —C(O)—$CO_{6-14}$aryl, v) —C(O)$NH_2$, w) —C(O)NH—$C_{1-20}$alkyl, x) —C(O)N($C_{1-20}$alkyl)$_2$, y) —C(O)NH—$C_{6-14}$aryl, z) —C(O)N($C_{1-20}$alkyl)-$C_{6-14}$aryl, aa) —C(O)N($C_{6-14}$aryl)$_2$, ab) —C(S)$NH_2$, ac) —C(S)NH—$C_{1-20}$alkyl, ad) —C(S)N($C_{1-20}$alkyl)$_2$, ae) —C(S)N($C_{6-14}$aryl)$_2$, af) —C(S)N($C_{1-20}$alkyl)-$C_{6-14}$aryl, ag) —C(S)NH—$C_{6-14}$ aryl, ah) —S(O)$_m NH_2$, ai) —S(O)$_m$NH($C_{1-20}$alkyl), aj) —S(O$_m$N($C_{1-20}$alkyl)$_2$, ak) —S(O)$_m$NH ($C_{6-14}$aryl), al) —S(O)$_m$N($C_{1-20}$alkyl)-$C_{6-14}$aryl, am) —S(O)$_m$N($C_{6-14}$aryl)$_2$, an) —$SiH_3$, ao) —SiH($C_{1-20}$alkyl)$_2$, ap) —$SiH_2$($C_{1-20}$alkyl), ar) —Si($C_{1-20}$alkyl)$_3$, as) a $C_{1-20}$alkoxy group, at) a $C_{2-20}$alkenyl group, au) a $C_{2-20}$alkynyl group, av) a $C_{1-20}$alkoxy group, aw) a $C_{1-20}$alkylthio group, ax) a $C_{1-20}$haloalkyl group, ay) a $C_{3-14}$cycloalkyl group, az) a $C_{6-14}$aryl group, ba) a 3-14 membered cycloheteroalkyl group, or bb) a 5-14 membered heteroaryl group;

Y, at each occurrence, is a) a divalent $C_{1-20}$ alkyl group, b) a divalent $C_{1-20}$ haloalkyl group, or c) a covalent bond;
m, at each occurrence, is 0, 1, or 2 and
q, at each occurrence, is an integer in the range of 1 to 20,
L is —$(Ar^2)$—, wherein $Ar^2$ is selected from the group consisting of:
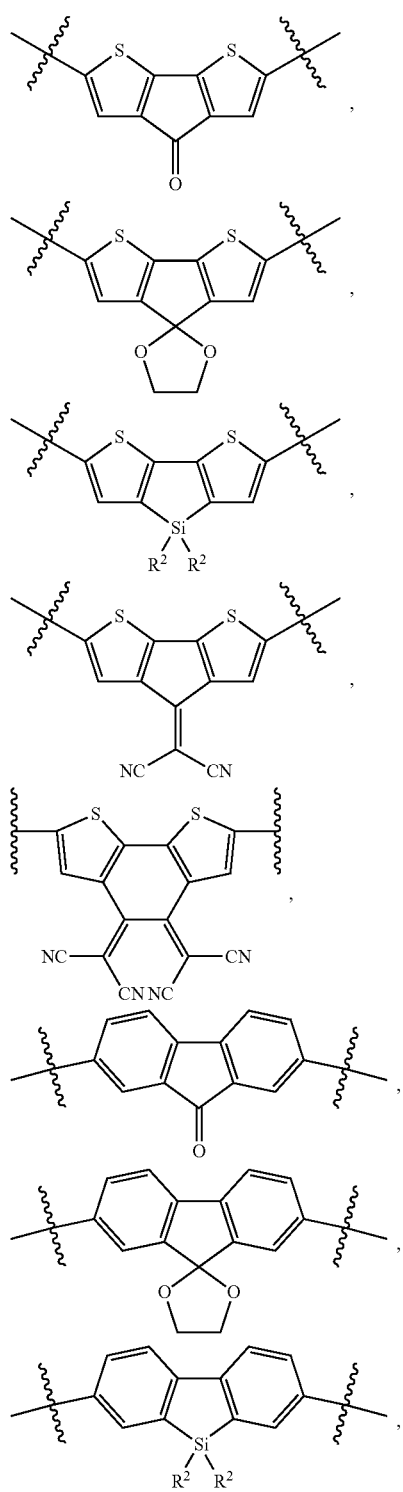
-continued
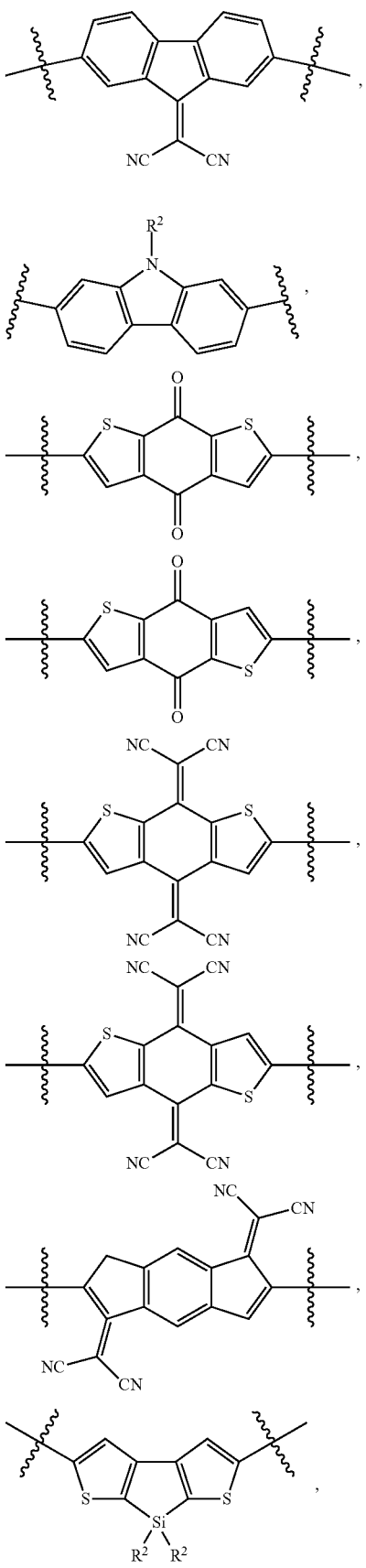

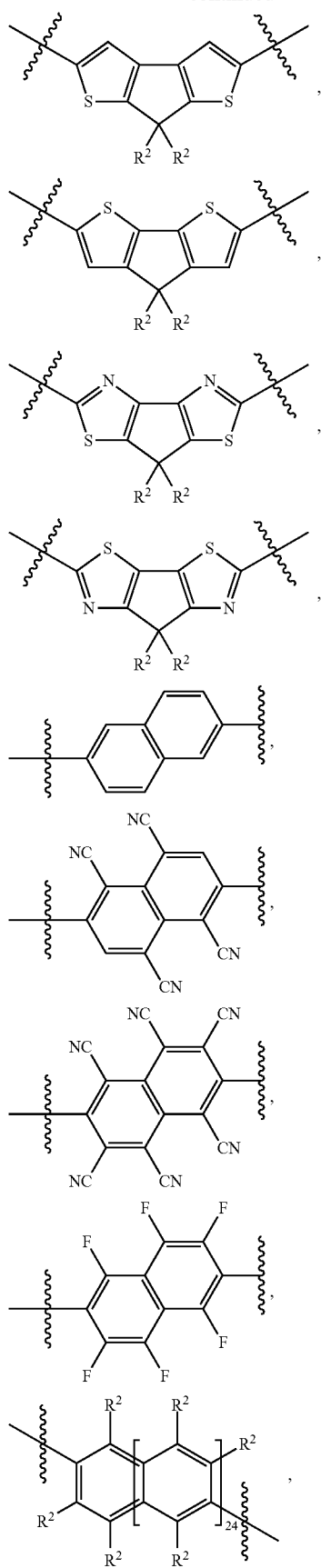
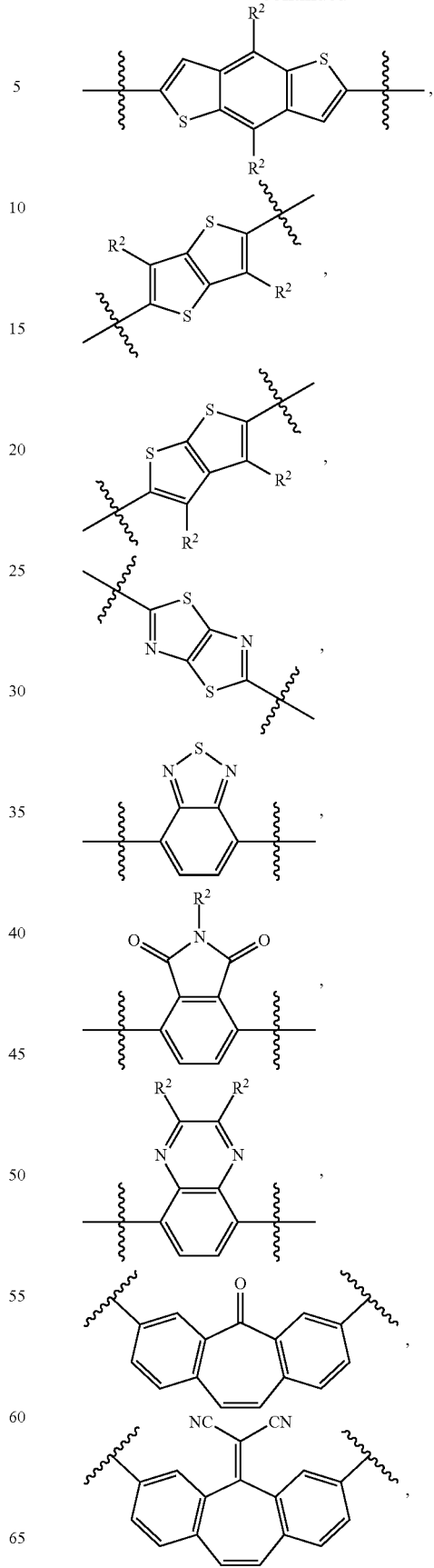

-continued

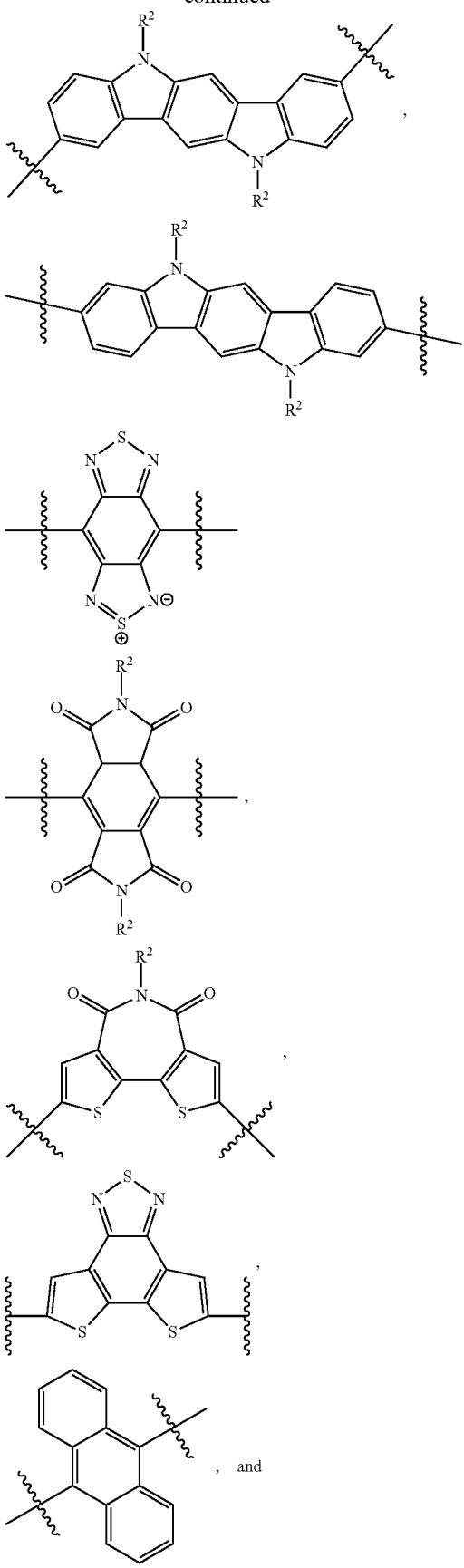

, and

-continued

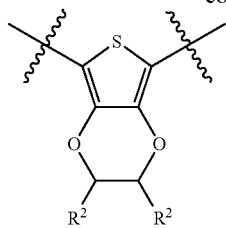

, wherein R², at each occurrence, independently is H or R$^i$.

4. A compound having Formula I:

Q-L-Q'    I, wherein:
Q and Q' independently are:

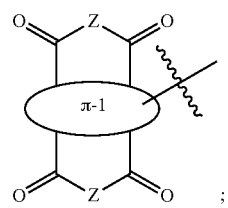

;

and
wherein:
π-1 is a perylene moiety optionally substituted with 1-8 R$^a$ groups;
Z, at each occurrence, is selected from the group consisting of a) O, b) S, c) NR$^b$, d) C(O), and e) CR$^c$R$^d$;
R$^a$, at each occurrence, is a) halogen, b) —CN, c) —NO$_2$, d) —OR$^f$, e) —SR$^f$, f) —NR$^g$R$^h$, g) —N(O)R$^g$R$^h$, h) —S(O)$_m$R$^g$, i) —S(O)$_m$OR$^g$, j) —S(O)$_m$NR$^g$R$^h$, k) —C(O)R$^g$, l) —C(O)OR$^f$, m) —C(O)NR$^g$R$^h$, n) —C(S)NR$^g$R$^h$, o) —SiH$_3$, p) —SiH(C$_{1-20}$alkyl)$_2$, q) —SiH$_2$(C$_{1-20}$alkyl), r) —Si(C$_{1-20}$alkyl)$_3$, s) a C$_{1-20}$alkyl group, t) a C$_{2-20}$alkenyl group, u) a C$_{2-20}$alkynyl group, v) a C$_{1-20}$haloalkyl group, w) a —Y—C$_{3-14}$cycloalkyl group, x) a —Y—C$_{6-14}$aryl group, y) a —Y-3-14 membered cycloheteroalkyl group, or z) a —Y-5-14 membered heteroaryl group, wherein each of the C$_{1-20}$alkyl group, the C$_{2-20}$alkenyl group, the C$_{2-20}$alkynyl group, the C$_{3-14}$cycloalkyl group, the C$_{6-14}$aryl group, the 3-14 membered cycloheteroalkyl group, and the 5-14 membered heteroaryl group optionally is substituted with 1-4 R$^i$ groups;
R$^b$, at each occurrence, is a) H, b) —(CH$_2$CH$_2$O)$_q$H, c) —(CH$_2$CH$_2$O)$_q$—CH$_3$, d) —C(O)OR$^f$, e) —C(O)R$^g$, f) —C(O)NR$^g$R$^h$, g) —C(S)OR$^f$, h) —C(S)R$^g$, i) —C(S)NR$^g$R$^h$, j) —S(O)$_m$R$^g$, k) —S(O)$_m$OR$^g$, l) a C$_{1-20}$alkyl group, m) a C$_{2-20}$alkenyl group, n) a C$_{2-20}$alkynyl group, o) a C$_{1-20}$alkoxy group, p) a —Y—C$_{3-14}$cycloalkyl group, q) a —Y—C$_{6-14}$aryl group, r) a —Y-3-14 membered cycloheteroalkyl group, or s) a —Y-5-14 membered heteroaryl group, wherein each of the C$_{1-20}$alkyl group, the C$_{2-20}$alkenyl group, the C$_{2-20}$alkynyl group, the C$_{1-20}$alkoxy group, the C$_{3-14}$cycloalkyl group, the C$_{6-14}$aryl group, the 3-14 membered cycloheteroalkyl group, and the 5-14 membered heteroaryl group optionally is substituted with 1-4 R$^i$ groups;

$R^c$ and $R^d$, at each occurrence, independently are a) H, b) halogen, c) —(CH$_2$CH$_2$O)$_q$H, d) —(CH$_2$CH$_2$O)$_q$—CH$_3$, e) a C$_{1-20}$alkoxy group, f) a C$_{1-20}$alkyl group, g) a C$_{2-20}$alkenyl group, h) a C$_{2-20}$alkynyl group, i) a —Y—C$_{3-14}$cycloalkyl group, j) a —Y—C$_{6-14}$aryl group, k) a —Y-3-14 membered cycloheteroalkyl group, or l) a —Y-5-14 membered heteroaryl group, wherein each of the C$_{1-20}$alkyl group, the C$_{2-20}$alkenyl group, the C$_{2-20}$alkynyl group, the C$_{3-14}$cycloalkyl group, the C$_{6-14}$aryl group, the 3-14 membered cycloheteroalkyl group, and the 5-14 membered heteroaryl group optionally is substituted with 1-4 $R^i$ groups;

$R^f$, at each occurrence, is a) H, b) —C(O)R$^g$, c) —C(O)NR$^g$R$^h$, d) —C(S)R$^g$, e) —C(S)NR$^g$R$^h$, f) a C$_{1-20}$alkyl group, g) a C$_{2-20}$alkenyl group, h) a C$_{2-20}$alkynyl group, i) a C$_{3-14}$cycloalkyl group, j) a C$_{6-14}$aryl group, k) a 3-14 membered cycloheteroalkyl group, or l) a 5-14 membered heteroaryl group, wherein each of the C$_{1-20}$alkyl group, the C$_{2-20}$alkenyl group, the C$_{2-20}$alkynyl group, the C$_{3-14}$cycloalkyl group, the C$_{6-14}$ aryl group, the 3-14 membered cycloheteroalkyl group, and the 5-14 membered heteroaryl group optionally is substituted with 1-4 $R^i$ groups;

$R^g$ and $R^h$, at each occurrence, independently are a) H, b) —OH, c) —SH, d) —S(O)$_2$OH, e) —C(O)OH, f) —C(O)NH$_2$, g) —C(S)NH$_2$, h) —OC$_{1-10}$alkyl, i) —C(O)—C$_{1-20}$ alkyl, j) —C(O)—OC$_{1-20}$alkyl, k) —C(S)N(C$_{1-20}$alkyl)$_2$, l) —C(S)NH—C$_{1-20}$alkyl, m) —C(O)NH—C$_{1-20}$alkyl, n) —C(O)N(C$_{1-20}$alkyl)$_2$, o) —S(O)$_m$—C$_{1-20}$alkyl, p) —S(O)$_m$—OC$_{1-20}$ alkyl, q) a C$_{1-20}$alkyl group, r) a C$_{2-20}$alkenyl group, s) a C$_{2-20}$alkynyl group, t) a C$_{1-20}$ alkoxy group, u) a C$_{3-14}$cycloalkyl group, v) a C$_{6-14}$aryl group, w) a 3-14 membered cycloheteroalkyl group, or x) a 5-14 membered heteroaryl group, wherein each of the C$_{1-20}$alkyl groups, the C$_{2-20}$alkenyl group, the C$_{2-20}$alkynyl group, the C$_{3-14}$ cycloalkyl group, the C$_{6-14}$aryl group, the 3-14 membered cycloheteroalkyl group, and the 5-14 membered heteroaryl group optionally is substituted with 1-4 $R^i$ groups;

$R^i$, at each occurrence, is a) halogen, b) —CN, c) —NO$_2$, d) oxo, e) —OH, f) —NH$_2$, g) —NH(C$_{1-20}$ alkyl), h) —N(C$_{1-20}$alkyl)$_2$, i) —N(C$_{1-20}$alkyl)-C$_{6-14}$ aryl, j) —N(C$_{6-14}$aryl)$_2$, k) —S(O)$_m$H, l) —S(O)$_m$—C$_{1-20}$alkyl, m) —S(O)$_2$OH, n) —S(O)$_m$—OC$_{1-20}$ alkyl, o) —S(O)$_m$—OC$_{6-14}$aryl, p) —CHO, q) —C(O)—C$_{1-20}$alkyl, r) —C(O)-C$_{6-14}$aryl, s) —C(O)OH, t) —C(O)—OC$_{1-20}$alkyl, u) —C(O)—OC$_{6-14}$ aryl, v) —C(O)NH$_2$, w) —C(O)NH—C$_{1-20}$alkyl, x) —C(O)N(C$_{1-20}$alkyl)$_2$, y) —C(O)NH—C$_{6-14}$aryl, z) —C(O)N(C$_{1-20}$alkyl)-C$_{6-14}$aryl, aa) —C(O)N(C$_{6-14}$ aryl)$_2$, ab) —C(S)NH$_2$, ac) —(C(S)NH—C$_{1-20}$alkyl, ad) —C(S)N(C$_{1-20}$alkyl)$_2$, ae) —C(S)N(C$_{6-14}$aryl)$_2$, af) —C(S)N(C$_{1-20}$alkyl)-C$_{6-14}$aryl, ag) —C(S)NH—C$_{6-14}$ aryl, ah) —S(O)$_m$NH$_2$, ai) —S(O)$_m$NH(C$_{1-20}$ alkyl), aj) —S(O$_m$N(C$_{1-20}$alkyl)$_2$, ak) —S(O)$_m$NH(C$_{6-14}$aryl), al) —S(O)$_m$N(C$_{1-20}$alkyl)-C$_{6-14}$aryl, am) —S(O)$_m$N(C$_{6-14}$aryl)$_2$, an) —SiH$_3$, ao) —SiH(C$_{1-20}$ alkyl)$_2$, ap) —SiH$_2$(C$_{1-20}$alkyl), ar) —Si(C$_{1-20}$ alkyl)$_3$, as) a C$_{1-20}$alkoxy group, at) a C$_{2-20}$alkenyl group, au) a C$_{2-20}$alkynyl group, av) a C$_{1-20}$alkoxy group, aw) a C$_{1-20}$alkylthio group, ax) a C$_{1-20}$haloalkyl group, ay) a C$_{3-14}$cycloalkyl group, az) a C$_{6-14}$aryl group, ba) a 3-14 membered cycloheteroalkyl group, or bb) a 5-14 membered heteroaryl group;

Y, at each occurrence, is a) a divalent C$_{1-20}$alkyl group, b) a divalent C$_{1-20}$ haloalkyl group, or c) a covalent bond;

m, at each occurrence, is 0, 1, or 2 and q, at each occurrence, is an integer in the range of 1 to 20, L is

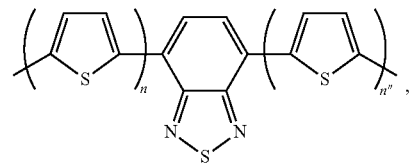

wherein each of n and n" is 1 or 2.

5. A compound of the formula:

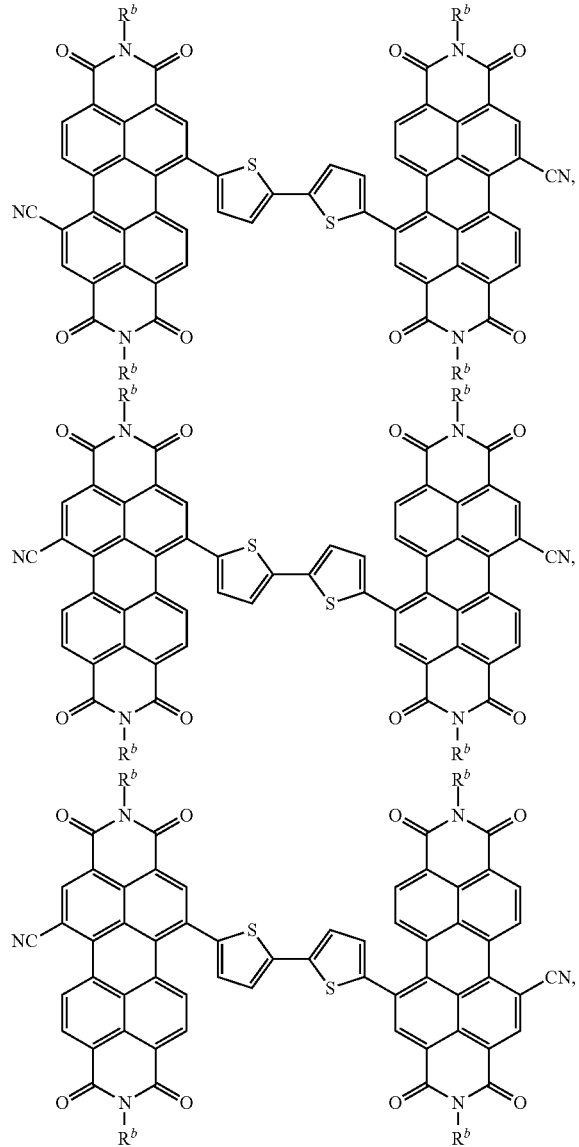

-continued

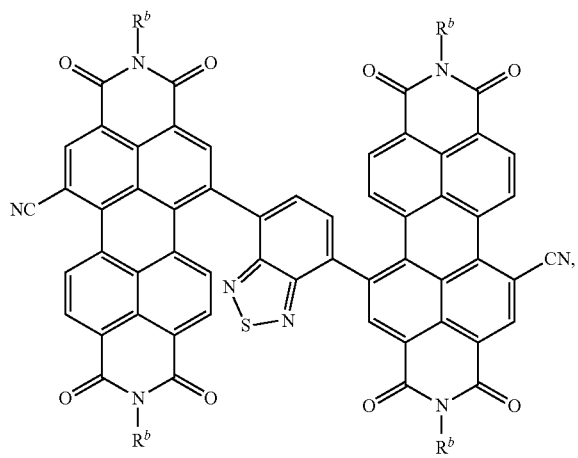

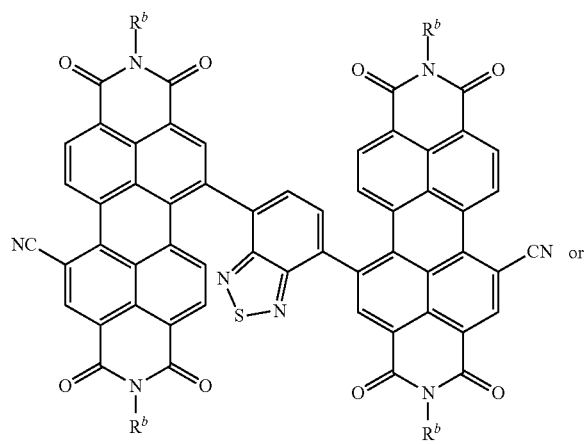

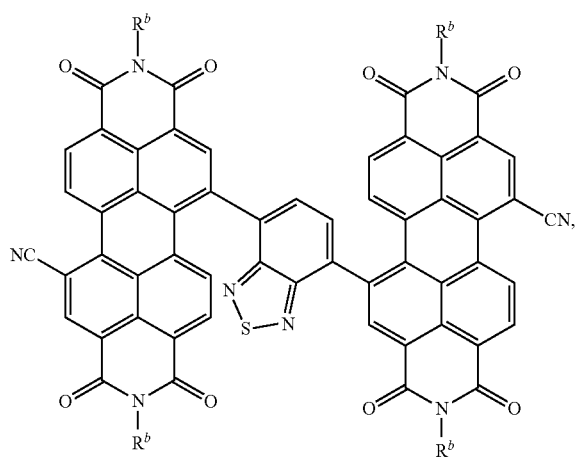

wherein $R^b$, at each occurrence, is a linear or branched $C_{4-20}$ alkyl group.

6. The compound of claim 1, wherein π-1, at each occurrence, is selected from the group consisting of:

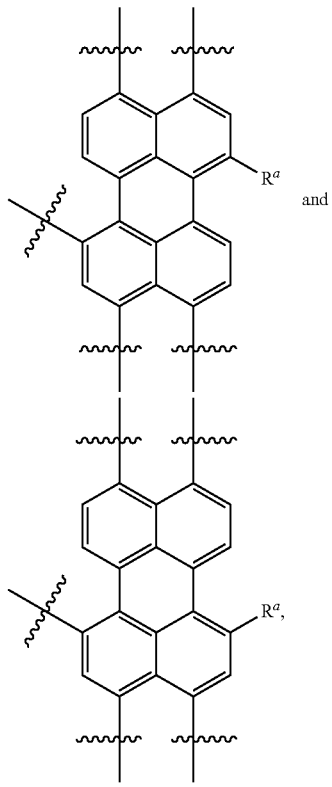

wherein each Z is O or $NR^b$.

7. A composition comprising one or more compounds of claim 1, dissolved or dispersed in a liquid medium.

8. An electronic, optical, or optoelectronic device comprising a thin film semiconductor comprising one or more compounds of claim 1.

9. A method of making an electronic, optical, or optoelectronic device, the device comprising a thin film conductor, the method comprising depositing a composition of claim 7 onto a substrate, wherein depositing the composition comprises at least one selected from the group consisting of printing, spin coating, drop-casting, zone casting, dip coating, blade coating, and spraying.

10. The compound of claim 2, wherein π-1, at each occurrence, is selected from the group consisting of:

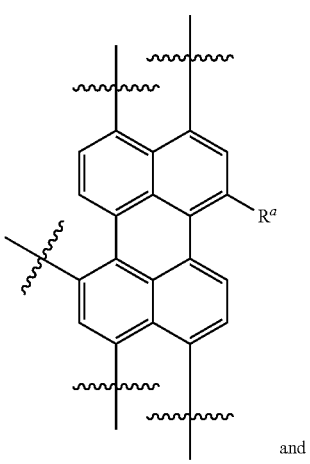

and

-continued

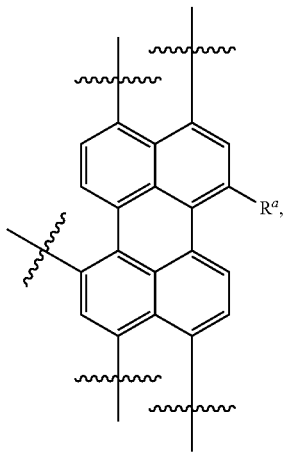

wherein each Z is O or NR$^b$.

11. A composition comprising one or more compounds of claim 2, dissolved or dispersed in a liquid medium.

12. An electronic, optical, or optoelectronic device comprising a thin film semiconductor comprising one or more compounds of claim 2.

13. A method of making an electronic, optical, or optoelectronic device, the device comprising a thin film conductor, the method comprising depositing a composition of claim 11 onto a substrate, wherein depositing the composition comprises at least one selected from the group consisting of printing, spin coating, drop-casting, zone casting, dip coating, blade coating, and spraying.

14. The compound of claim 3, wherein π-1, at each occurrence, is selected from the group consisting of:

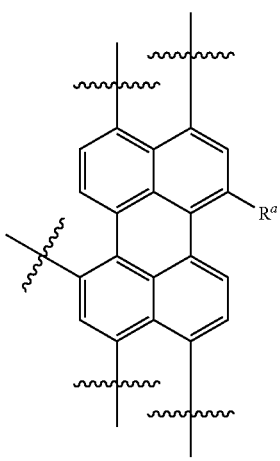

and

-continued

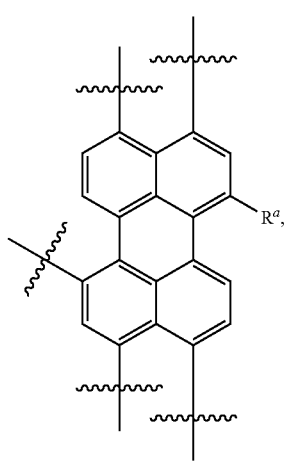

wherein each Z is O or NR$^b$.

15. A composition comprising one or more compounds of claim 3, dissolved or dispersed in a liquid medium.

16. An electronic, optical, or optoelectronic device comprising a thin film semiconductor comprising one or more compounds of claim 3.

17. A method of making an electronic, optical, or optoelectronic device, the device comprising a thin film conductor, the method comprising depositing a composition of claim 15 onto a substrate, wherein depositing the composition comprises at least one selected from the group consisting of printing, spin coating, drop-casting, zone casting, dip coating, blade coating, and spraying.

18. The compound of claim 4, wherein π-1, at each occurrence, is selected from the group consisting of:

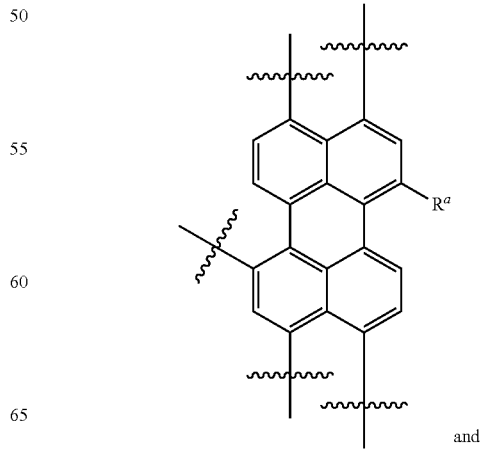

and

-continued

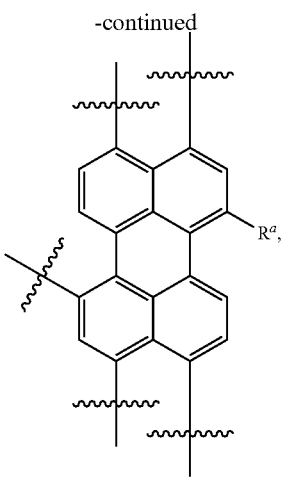

wherein each Z is O or $NR^b$.

19. A composition comprising one or more compounds of claim 4, dissolved or dispersed in a liquid medium.

20. An electronic, optical, or optoelectronic device comprising a thin film semiconductor comprising one or more compounds of claim 4.

21. A method of making an electronic, optical, or optoelectronic device, the device comprising a thin film conductor, the method comprising depositing a composition of claim 19 onto a substrate, wherein depositing the composition comprises at least one selected from the group consisting of printing, spin coating, drop-casting, zone casting, dip coating, blade coating, and spraying.

22. A composition comprising one or more compounds of claim 5, dissolved or dispersed in a liquid medium.

23. An electronic, optical, or optoelectronic device comprising a thin film semiconductor comprising one or more compounds of claim 5.

24. A method of making an electronic, optical, or optoelectronic device, the device comprising a thin film conductor, the method comprising depositing a composition of claim 22 onto a substrate, wherein depositing the composition comprises at least one selected from the group consisting of printing, spin coating, drop-casting, zone casting, dip coating, blade coating, and spraying.

* * * * *